(12) United States Patent
Gordeev et al.

(10) Patent No.: US 9,382,276 B2
(45) Date of Patent: Jul. 5, 2016

(54) WATER-SOLUBLE O-CARBONYL PHOSPHORAMIDATE PRODRUGS FOR THERAPEUTIC ADMINISTRATION

(71) Applicant: MicuRx Pharmaceuticals, Inc., Hayward, CA (US)

(72) Inventors: Mikhail Fedorovich Gordeev, Castro Valley, CA (US); Jinqian Liu, Fremont, CA (US); Xinghai Wang, Shanghai (CN); Zhengyu Yuan, Palo Alto, CA (US)

(73) Assignee: MicuRx Pharmaceuticals, Inc., Hayward, CA (US)

( * ) Notice: Subject to any disclaimer, the term of this patent is extended or adjusted under 35 U.S.C. 154(b) by 0 days.

(21) Appl. No.: 14/628,134

(22) Filed: Feb. 20, 2015

(65) Prior Publication Data
US 2015/0239922 A1    Aug. 27, 2015

Related U.S. Application Data

(60) Provisional application No. 61/943,129, filed on Feb. 21, 2014.

(51) Int. Cl.
| | | |
|---|---|---|
| C07F 9/653 | (2006.01) | |
| C07F 9/6558 | (2006.01) | |
| C07F 9/6561 | (2006.01) | |
| C07F 9/6574 | (2006.01) | |
| A61K 31/42 | (2006.01) | |
| A61K 31/664 | (2006.01) | |

(52) U.S. Cl.
CPC ............ *C07F 9/65583* (2013.01); *C07F 9/653* (2013.01); *C07F 9/6561* (2013.01); *C07F 9/65742* (2013.01)

(58) Field of Classification Search
None
See application file for complete search history.

(56) References Cited

U.S. PATENT DOCUMENTS

| | | |
|---|---|---|
| 5,668,286 A | 9/1997 | Yamada et al. |
| 6,417,175 B1 | 7/2002 | Ishikawa et al. |
| 6,906,055 B2 | 6/2005 | Ishikawa et al. |
| 6,919,329 B2 | 7/2005 | Thomas et al. |
| 7,105,547 B2 | 9/2006 | Gordeev et al. |
| 7,141,588 B2 | 11/2006 | Thomas et al. |
| 7,588,690 B1 | 9/2009 | Tsao |
| 8,178,683 B2 | 5/2012 | Gordeev et al. |
| 2004/0059120 A1 | 3/2004 | Natesan et al. |
| 2010/0069441 A1 | 3/2010 | Gordeev et al. |
| 2010/0204477 A1 | 8/2010 | Wang et al. |
| 2012/0065170 A1 | 3/2012 | Gordeev et al. |
| 2012/0157434 A1 | 6/2012 | Gordeev et al. |

FOREIGN PATENT DOCUMENTS

| | | |
|---|---|---|
| EP | 1683803 | 7/2006 |
| WO | WO 97/35864 | 10/1997 |
| WO | WO/99/32497 | 1/1999 |
| WO | WO 00/21960 | 4/2000 |
| WO | WO 03/006440 | 1/2003 |
| WO | WO 03/072553 | 9/2003 |
| WO | WO 2004/033449 | 4/2004 |
| WO | WO 2004/056816 | 7/2004 |
| WO | WO 2004/087697 | 10/2004 |
| WO | WO 2005/019213 | 3/2005 |
| WO | WO 2005/028473 | 3/2005 |
| WO | WO 2005/058886 | 6/2005 |
| WO | WO 2005/113520 | 12/2005 |
| WO | WO 2006/038100 | 4/2006 |
| WO | WO 2006/043121 | 4/2006 |
| WO | WO 2007/000644 | 1/2007 |
| WO | WO 2007/004049 | 1/2007 |
| WO | WO 2009/020616 | 2/2009 |
| WO | WO 2009/020616 A1 * | 2/2009 |
| WO | WO 2010/121021 | 10/2010 |
| WO | WO 2011/088030 | 7/2011 |

OTHER PUBLICATIONS

Ishikawa et al, Bioorganic & Medicinal Chemisry, (2003) 11, pp. 2427-2437.*
International Search Report and Written Opinion for PCT/US2015/0016970, mailed May 7, 2015, 13 pgs.
Alexander et al., "(Acyloxy)alkyl Carbamate Prodrugs of Norfloxacin", J. Med. Chem., vol. 34, No. 1 pp. 78-81(1991).
Alexander et al., "(Acyloxy) alkyl Carbamates as Novel Bioreversible Prodrugs for Amines: Increased Permeation through Biological Membranes", J. Med. Chem. vol. 31, pp. 318-322 (1988).
Benkovic et al., "Structure-Reactivity Correlation for the Hydrolysis of Phosphoramidate Monoanions", J. of the Amer. Chem. Soc., vol. 93, pp. 4009-4016 (1971).
Davidsen et al., "N-(Acyloxyalkyl) pyridinium Salts as Soluble Prodrugs of a Potent Platelet Activating Factor Antagonist", J. of Med. Chem. vol. 37, No. 26, pp. 4423-4429 (1994).
Ettmayer et al., "Lessons Learned from Marketed and Investigational Prodrugs", J. Med. Chem., vol. 47, No. 10, pp. 2393-2404 (2004).

(Continued)

*Primary Examiner* — Zinna Northington Davis
(74) *Attorney, Agent, or Firm* — Squire Patton Boggs (US) LLP

(57) ABSTRACT

The present invention provides certain water-soluble O-carbonyl phosphoramidate prodrugs of the following formula I:

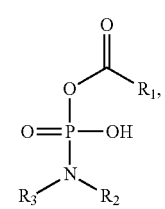

or pharmaceutically acceptable salts thereof that are therapeutic or antibacterial agents, pharmaceutical compositions containing them, methods for their use, and reagents and methods for preparing these compounds.

19 Claims, No Drawings

(56) References Cited

OTHER PUBLICATIONS

Ge et al., "Comparative Pharmacokinetics of Ceftaroline in Rats, Rabbits, and Monkeys following a Single Intravenous of Intramuscular Injection", Antimicrob. Agents Chemotherapy vol. 54, No. 2, pp. 912-914 (2010).
Gordeev et al, "New Potent Antibacterial Oxazolidinone (MRX-1) with an Improved Class Safety Profile", J. Med. Chem. vol. 57, pp. 4487-4497 (2014).
Guarino et al., "Sulfenamides as prodrugs of NH-acidic compounds: A new prodrug option for the amide bond", Bioorganic Medicinal. Chem. Lett. 17, pp. 4910-4913 (2007).
Ishikawa et al., "TAK-599, a novel N-phosphono type prodrug of anti-MRSA cephalosporin 1-91825: synthesis, physicochemical and pharmacological properties", Bioorganic & Medicinal Chemistry, Pergamon, GB, vol. 11, No. 11, pp. 2427-2437 (2003).
Keyes et al., "Correlation of Anti-HIV Potency with Lipophilicity in a Series of Cosalane Analogs Having Normal Alkenyl and Phosphodiester Chains as Cholestane Replacements", J. Med. Chem. 39, pp. 508-514 (1996).
Krise et al., "Novel Prodrug Approach for Tertiary Amines: Synthesis and Preliminary Evaluation of N-Phosphonooxymethyl Prodrugs", J. Med. Chem. 42, pp. 3094-3100 (1999).
Kuz'min et al., "Phophorus-Containing Aminoisoxazoles", Zhurnal Obshchei Khimii (J. of General Chemistry of the USSR) vol. 60, pp. 1729-1832 (1990).
Modro et al., "The mechanism of phosphoryl to carbonyl migration of amino groups in mixed anhydrides. A MNDO SCF-MO study", J. of the Chem. Soc., Perkin Trans. 2, No. 6, p. 767 (1987).
Murdock et al., "N-Phosphoryl Derivatives of Bisantrene. Antitumor Prodrugs with Enhanced Solubility and Reduced Potential for Toxicity", J. Med. Chem., 36, pp. 2098-2101(1993).
Ohwada et al., "Design, Synthesis and Antifungal Activity of a Novel Water Soluble Prodrug of Antifungal Triazole", Bioorgan. Medicinal. Chem. Lett. 13, pp. 191-196 (2003).
Rahmathullah et al., "Prodrugs for Amidines: Synthesis and Anti-Pneumocystic Carinii Activity of Carbamates of 2,5-Bis(4-amidinophenyl)furan", J. Med. Chem. 42, pp. 3994-4000 (1999).
Raicu et al., "Cytogenetic investigations on two new alkylating agents", Mech. Mutat. Inducing Factors, Proc. Symp., Meeting Date 1965, pp. 371-376, Publisher: Academia, Prague, Czech. Rep (English abstract only).
Robinson et al., "Discovery of the Hemifumarate and (α-L-Alanyloxy) methyl Ether as Prodrugs of an Antirheumatic Oxindole: Prodrugs for the Enolic OH Group", J. Med. Chem. 39, pp. 10-18 (1996).
Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage", J. Med. Chem. 46, pp. 4124-4135 (2003).
Stella et al., "Prodrug strategies to overcome poor water solubility", Adv. Drug Delivery Rev. 59, pp. 677-694 (2007).
Sun et al.,"Synthesis and Evaluation of Oxodioxolenylmethyl Carbamate Prodrugs of Pseudomycins", J. Med. Chem. 44, pp. 2671-2674 (2001).
Zhu et al., "Phosphate Prodrugs of PD154075", Bioorg. Med. Chem. Lett. 10, pp. 1121-1124 (2000).
Humphrey et. al., "Cardiovascular Sympathomimetic Amine Interactions in Rats Treated with Monoamine Oxidase Inhibitors and the Novel Oxazolidinone Antibiotic Linezolid", *Journal of Cardiovascular Pharmacology*, (2001) 37:548-563.
Hutchinson D.K., "Oxazolidinone Antibacterial Agents: A Critical Review", *Current Topics in Medicinal Chemistry*, (2003) 3:1021-1042.
Jones et al., "Zyvox® Annual Appraisal of Potency and Spectrum program: linezolid surveillance program results for 2008", *Diagnostic Microbiology and Infectious Disease*, (2009) 65:404-413.
Miller, Robert F. "Cell Communication Mechanisms in the Vertebrate Retina", *Investigative Ophthalmology & Visual Science*, Dec. 2008, vol. 49, No. 12.
Mutnick et al., "Spectrum and potency evaluation of a new oxazolidinone, linezolid: report from the SENTRY Antimicrobial Surveillance Program, 1998-2000", *Diagnostic Microbiology and Infectious Disease*, (2002) 43:65-73.
Nawy et al., "The glutamate analog 2-amino-4-phosphonobutyrate antagonizes synaptic transmission from cones to horizontal cells in goldfish retina", Proc. Natl. Acad. Sci USA vol. 86, pp. 1726-1730 Mar. 1989.
Park et al., "Antibacterials. Synthesis and Structure—Activity Studies of 3-Aryl-2-oxooxazolidines. 4. Multiply-Substituted Aryl Derivatives", *J. Med. Chem.*, (1992) 35:1156-1165.
Patani et. al., "Bioisosterism: A Rational Approach in Drug Design", *Chemical Reviews*, (1996) 96:3147-3176.
Prescribing Information for Zyvox, Jun. 2010, Pfizer LAB-0139-20.0, retrieved from U.S. Food & Drug Administration website.
Prescribing Information for Zyvox, Mar. 2007, Pfizer LAB-0139-16.0, retrieved from U.S, Food & Drug Administration website.
Renslo A.R., "Antibacterial oxazolidinones: emerging structure—toxicity relationships", *Expert Rev. Anti Infect. Ther.* (2010) 8(5):565-574.
Sawhney, S. K. and Singh, R. "Introductory Practical Biochemistry", *Narosa*: New Delhi, (2002) pp. 2-3.
Vinh et al., "Linezolid: a review of safety and tolerability", Journal of Infection, (2009) 59(S1):S59-S74.
Wakefield, B., "Fluorinated Pharmaceuticals", *Innovations in Pharmaceutical Technology*, (2000) 74:76-78.

\* cited by examiner

WATER-SOLUBLE O-CARBONYL PHOSPHORAMIDATE PRODRUGS FOR THERAPEUTIC ADMINISTRATION

CROSS REFERENCE

This application claims priority to U.S. Provisional Application No. 61/943,129 filed Feb. 21, 2014. The contents of this provisional application are hereby incorporated by reference in its entirety for all purposes.

FIELD OF THE INVENTION

Provided are novel O-carbonyl phosphoramidate prodrug derivatives of therapeutic agents and bioactive compounds, pharmaceutical compositions thereof, methods for their use, and reagents and methods for preparing of the same. These compounds are particularly suitable for therapeutic administration in a liquid drug form.

BACKGROUND OF THE INVENTION

Poor solubility of therapeutic agents is widely recognized as a serious issue that limits the effective administration of such compounds to the mammal in need thereof. One common approach to manage this problem is chemical derivatization of the compounds to form a prodrug, i.e. drug derivative that releases the parent active entity upon its administration, as reviewed, for example, by Ettmayer et al. in J. Med. Chem., 2004, p. 2393.

A limited number of effective prodrugs are known for NH-containing compounds, as noted, for example, by Stella et al. in Bioorg. Med. Chem. Lett., 2007, p. 4910. Amongst antibacterial agents, the prodrug of antibiotic ceftaroline, ceftaroline fosamil (described, for example, by Ge et al. in Antimicrob. Agents Chemotherapy, 2010, p. 912), is an example of a sole approved prodrug of the phosphoramidate class of N-phosphorylated amines.

Among newer antibacterials, oxazolidinone compounds are a class of antimicrobials active against all key gram-positive pathogens. Representative antibacterial agents of this class include linezolid (Zyvox$^R$), which is used for a treatment of key gram-positive infections.

As for many other pharmaceuticals, it is important that the oxazolidinone agent has sufficient solubility for its convenient administration in a liquid form. Thus, a modest solubility of linezolid requires a slow twice-daily intravenous infusion, since the single liquid drug dose of 600 mg is formulated in a relatively large volume of 300 cc.

None of aforementioned publications specifically contemplates compounds provided herein, their beneficial physicochemical profiles, their combination therapies, or compositions thereof.

SUMMARY OF THE INVENTION

Publications PCT JP1998/005709, U.S. Pat. No. 6,417,175, PCT JP2001/006904, and U.S. Pat. No. 6,906,055 describe certain phosphoramidate prodrugs. These compounds all lack the O-carbonyl phosphoramidate prodrug group described herein.

Publications Zhurnal Obshchei Khimii. 1990, vol. 60, p. 1991, and PCT WO 9735864 describe preparation of certain diphenyl isoxazol-3-ylphosphoramidates generally related to certain intermediates used for preparation of compounds provided herein.

Several publications describe potent antimicrobial oxazolidinones which incorporate (isoxazole-3-yl)aminomethyl groups. See, for example, PCT publications WO 2000/021960, WO 2004/056816, WO 2006/043121, and WO 2009/020616.

In particular, an oxazolidinone agent MRX-I is described in WO 2009/020616 and in J. Med. Chem. 2014, vol. 57, p. 4487 (see the structure below).

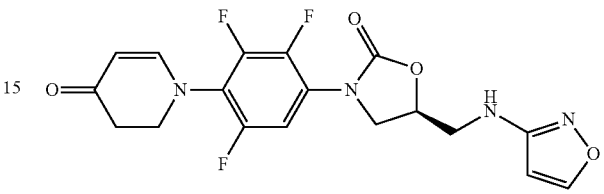

MRX-I

While this agent demonstrated a promising clinical potential as an oral agent for therapy use in a powder, suspension, or a tablet form, it has a modest aqueous solubility of about 0.25 mg/mL. Thus, a specialized soluble formulation composition would be required for administration of the agent MRX-I in its liquid form, which is needed, for example, for an injection or an infusion.

Importantly, the (isoxazole-3-yl)amino group featured in the above structure differs drastically from conventional basic amines. Indeed, the former group is almost entirely non-basic due to the unique electron-deficient nature of the isoxazole heterocycle. Consequently, the modest solubility of the agent MRX-I in water is virtually pH-independent, at least within the pH range of about 3-9, which is preferred for injection solutions. As a result, it is not feasible to solubilize the agent MRX-I and similar (isoxazole-3-yl)aminomethyl oxazolidinones by forming stable pharmaceutical salts. Furthermore, the essentially neutral character of the NH-containing group present in its structure impedes facile incorporation of typical NH-prodrug groups, such as described, for example, by Stella et al. in Bioorg. Med. Chem. Lett., 2007, p. 4910.

Provided herein are O-carbonyl phosphoramidate prodrug derivatives of NH-containing compounds, including prodrug compounds of the antibacterial oxazolidinone class exemplified by MRX-I.

The compounds provided herein are highly soluble in water and permit a convenient drug administration in a liquid form, as well as in other forms, such as a solid tablet or a powder pill form. Upon administration to a subject in need of a treatment, these compounds can undergo a cleavage of the nitrogen-phosphorus bond in vivo, thus releasing an active drug entity to achieve the desired therapeutic effect.

The compounds described herein feature an O-carbonyl (such as O-acyl) phosphate fragment —P(=O)(OH)—O—C(=O)R$^1$ which is similar to mixed phosphate-carboxylate anhydrides. These mixed anhydrides exhibit high reactivity and are used for acyl transfer reactions, as described, for example, by McNulty in Tetrahedron, 2012, vol. 68, p. 5415. In surprising contrast, the prodrug derivatives described herein exhibit good hydrolytic stability in aqueous or water-based solutions, and are suitable for the administration to a mammal in need of therapy.

Typically, hydrolytically labile phosphoramidate derivatives commonly require isolation in a salt form under basic conditions (as described, for example, by Benkovic et al. in J. Amer. Chem. Soc., 1971, vol. 93, p. 4009). In contrast, the O-carbonyl phosphoramidate prodrugs described herein are sufficiently stable under mildly acidic or essentially neutral conditions, which are commonly preferred for therapeutic drug administrations.

Separate from solubility and stability improvements, the prodrug compounds described herein can offer additional benefits derived from a controlled or generally slower release of the active entity (such as MRX-I) from its respective O-carbonyl phosphoramidate prodrug. These benefits may include, for example, improved drug tolerability due to attenuated maximum drug concentration (as compared to an injection of the drug itself), an improved distribution throughout the body due to the enhanced solubility, and attenuated protein or tissue binding, and an optimized exposure to the released drug. Thus, the administration of a compound of formula I-IV could result in overall superior therapy outcome as compared to similar administration of the active entity in its parent (non-prodrug) form.

Prodrug compound of formula I-IV provided herein is useful for solubilization of bioactive compounds and therapeutic agents incorporating NH-containing or $NPO_3H_2$-containing therapeutic agents, such as, for example, anticancer, antibacterial, antiviral, antifungal, cardiovascular, antiinflammatory, immunomodulatory, or central nervous system agents. Certain compounds of formula I are particularly useful for solubilization of antibacterial agents for treatment of infections including, but not limited to, skin infections, soft tissue infections, bacteremia, respiratory tract infections, urinary tract infections, bone infections, and eye infections.

In one aspect, provided is a compound of formula I:

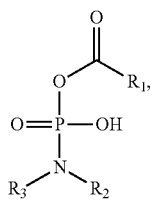

or a pharmaceutically acceptable salt thereof, wherein:
$R^1$ is H, $C_{1-20}$alkyl, $C_{3-6}$cycloalkyl, $C_{2-4}$alkenyl, $C_{2-4}$alkynyl, $C_{1-4}$heteroalkyl, aryl, heteroaryl, $Het^1$, $Het^2$, $C(=O)C_{1-4}$alkyl, $C(=O)OH$, $C(=O)OC_{1-4}$alkyl, $(CH_2)_mC(=O)OH$, $(CH_2)_mC(=O)C_{1-4}$alkyl, $(CH_2)_mC(=O)OC_{1-4}$alkyl, $NH_2$, $NHC_{1-4}$alkyl, $N(C_{1-4}$alkyl) $C_{1-4}$alkyl, $N(C_{1-4}$alkyl) aryl, $OC_{1-4}$alkyl, $SC_{1-4}$alkyl, $(CH_2)_mC_{3-6}$cycloalkyl, $(CH_2)_mC(=O)$-aryl, or $(CH_2)_mC(=O)$-$Het^1$, wherein m is 0, 1, or 2; and
$R^2$ and $R^3$ are independently selected from H, $C_{1-20}$alkyl, $C_{3-6}$cycloalkyl, $C_{2-4}$alkenyl, $C_{2-4}$alkynyl, $C_{1-20}$heteroalkyl, aryl, heteroaryl, [3-(2,3,5-trifluoro-4-(4-oxo-3,4-dihydropyridin-1(2H)-yl)phenyl)oxazolidin-2-one-5-yl]methyl, [3-(3-fluoro-4-morpholinophenyl)oxazolidin-2-one-5-yl]methyl, [3-(3-fluoro-4-(6-(2-methyl-2H-tetrazol-5-yl)pyridin-3-yl)phenyl) -oxazolidin-2-one-5-yl]methyl, [3-(3-fluoro-4-(6-(1-methyl-1H-tetrazol-5-yl) pyridin-3-yl)phenyl)-oxazolidin-2-one-5-yl]methyl, $Het^1$, $Het^2$, $C(=O)C_{1-4}$alkyl, $(CH_2)_mC(=O)C_{1-4}$alkyl, $(CH_2)_m C_{3-6}$cycloalkyl, $(CH_2)_mC(=O)$-aryl, and $(CH_2)_mC(=O)$-$Het^1$.

In certain aspects, $R^1$ in a compound of formula I is H or $CH_3$.

In certain aspects, $R^2$ in a compound of formula I is $C(=O)CH_3$ or isoxazol-3-yl.

In certain aspects, $NR^2R^3$ fragment in a compound of formula I is a group formed by removing NH-proton from a structure $N(H)R^2R^3$, wherein $N(H)R^2R^3$ is a compound for which a solubility improvement is desired.

In certain aspects, $R^3$ in a compound of formula I is [3-(2,3,5-trifluoro-4-(4-oxo-3,4-dihydropyridin-1(2H)-yl)phenyl)oxazolidin-2-one-5-yl]methyl, [3-(3-fluoro-4-morpholinophenyl)oxazolidin-2-one-5-yl]methyl, [3-(3-fluoro-4-(6-(2-methyl-2H-tetrazol-5-yl)pyridin-3-yl)phenyl)-oxazolidin-2-one-5-yl]methyl, or [3-(3-fluoro-4-(6-(1-methyl-1H-tetrazol-5-yl)pyridin-3-yl)phenyl)-oxazolidin-2-one-5-yl].

In another aspect, a compound of formula I is prodrug of linezolid, wherein $R^2$ is acetyl, and $R^3$ is [3-(3-fluoro-4-morpholinophenyl)oxazolidin-2-one-5-(S)-yl]methyl.

In another aspect, a compound of formula I is according to formula II:

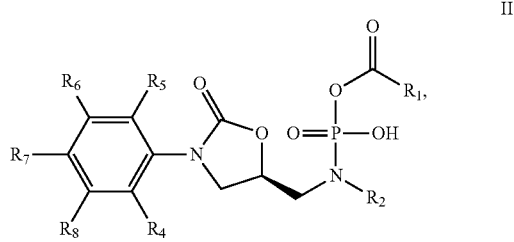

or a pharmaceutically acceptable salt thereof wherein:
$R^2$ is isoxazol-3-yl (optionally substituted with 1 $R^9$), $C(=O)C_{1-4}$alkyl, $(CH_2)_mC(=O)C_{1-4}$alkyl, $(CH_2)_mC_{3-6}$cycloalkyl, $(CH_2)_mC(=O)$-aryl, or $(CH_2)_mC(=O)$-$Het^1$, wherein m is 0, 1, or 2;
$R^4$ and $R^5$ are independently H or F; and
$R^6$ and $R^8$ are independently H, F, Cl, or CN; and
$R^7$ is $C_{3-6}$cycloalkyl, aryl, biaryl, $Het^1$, $Het^2$, or 4 to 7-membered heterocyclic group; or $R^6$ and $R^7$ taken together form a 4 to 7-membered heterocyclic group fused onto the benzene ring; and
$R^9$ is H, $C_{1-6}$alkyl, halo, or CN.

In certain aspects, $R^4$, $R^5$ $R^6$, and $R^8$ in a compound of formula II are independently selected from H or F, and $R^7$ is morpholino, 2,3-dihydropyridin-4(1H)-one-1-yl, 4-cyanopyridyl, 2-(2-methyl-2H-tetrazol-5-yl)pyridine-5-yl, 2-(1-methyl-1H-tetrazol-5-yl)pyridine-5-yl, 4-[N-(1H-1,2,3-triazol-5-yl)methylaminomethyl]phenyl, 1-methyl-1,4,5,6-tetrahydro-1,2,4-triazin-4-yl, or 5,6-dihydro-1,2,4-oxadiazin-4-yl.

In another aspect, provided is a compound of formula II according to formula III

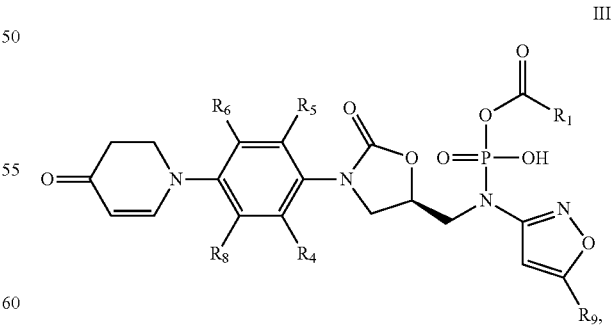

or a pharmaceutically acceptable salt thereof

In certain aspects, $R^1$ in a compound of formula I-III is $C_{1-8}$alkyl, $(CH_2)_mC(=O)OC_{1-4}$alkyl, $OC_{1-4}$alkyl, $NHC_{1-4}$alkyl, $N(C_{1-4}$alkyl) $C_{1-4}$alkyl, aryl, or $Het^2$, wherein m is 0, 1 or 2.

Also provided is a compound of formula IV

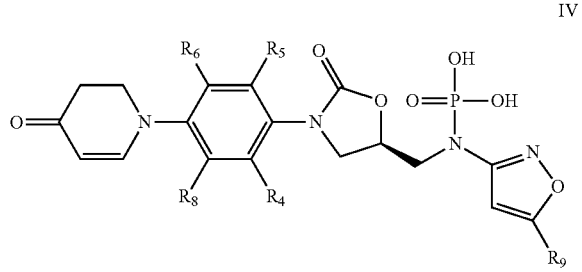

or a salt or solvate thereof, where
$R^4$ and $R^5$ are independently H or F; and
$R^6$ and $R^8$ are independently H, F, Cl, or CN; and
$R^7$ is $C_{3-6}$cycloalkyl, aryl, biaryl, Het$^1$, Het$^2$, or 4 to 7-membered heterocyclic group; or $R^6$ and $R^7$ taken together form a 4 to 7-membered heterocyclic group fused onto the benzene ring; and
$R^9$ is H, $C_{1-6}$alkyl, halo, or CN.

In certain aspects, $R^4$ and $R^9$ in a compound of formula IV are both H, and $R^5$, $R^6$, and $R^8$ are all F.

In one aspect, a compound of formula IV is useful for preparation of a compound of formula I-III.

In one aspect, a compound of formula IV is a prodrug for NH-containing pharmaceutical or bioactive agent of formula N(H)R$^2$R$^3$.

In another aspect, provided is a compound of formula V for preparation of a compound of any of formulas I-IV:

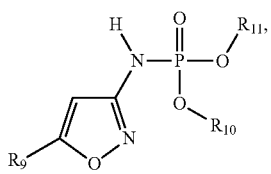

wherein:
$R^9$ is H, $C_{1-6}$alkyl, halo, or CN; and
$R^{10}$ and $R^{11}$ are independently selected from $C_{1-20}$alkyl and $C_{3-6}$cycloalkyl, or $R^{10}$ and $R^{11}$ taken together is $C_{1-20}$alkylidene group.

In certain aspects, $R^9$ in a compound of formula V is H, and both $R^{10}$ and $R^{11}$ are $C_{1-20}$alkyl.

In another aspect, the present invention provides a pharmaceutical composition comprising a compound of any of formulas I-IV, or a pharmaceutically acceptable salt thereof, and a pharmaceutically acceptable carrier.

In another aspect, the present invention provides a method for treating a microbial infection in a mammal by administering to the mammal in need a therapeutically effective amount of a compound provided herein, for example a compound of any of formulas I-IV, or a pharmaceutically acceptable salt thereof.

In another aspect, the present invention provides a method for the treatment of a microbial infection in a mammal comprising administering to the mammal in need thereof a therapeutically effective amount of a compound provided herein, for example a compound of any of formulas I-IV, or a pharmaceutically acceptable salt thereof.

In certain aspects, the microbial infection is a gram-positive microbial infection.

In certain aspects, the microbial infection is a gram-negative microbial infection.

In certain aspects, the microbial infection is a *Mycoplasma tuberculosis* infection.

The compounds described herein, for example a compound of any of formulas I-IV, may be administered orally, parenterally, transdermally, topically, rectally, or intranasally.

The compounds described herein, for example a compound of any of formulas I-IV, may be administered once-daily in an amount of from about 1 to about 75 mg/kg of body weight/day.

In certain aspects, the compounds provided herein are administered as water-based solutions thereof, at concentrations from about 20 to about 400 mg/mL.

In certain aspects, the compounds provided herein are administered as water-based solutions thereof, at concentration from about 50 to about 150 mg/mL.

In certain aspects, provided herein is a compound described herein, for example a compound of any of formulas I-IV, for use in therapy.

In certain aspects, provided herein is a compound described herein, for example a compound of any of formulas I-IV, for use in the treatment of a microbial infection in a mammal in need thereof.

In certain aspects, provided herein is use of a compound described herein, for example a compound of any of formulas I-IV, in the manufacture of a medicament for therapy.

In certain aspects, provided herein is use of a compound described herein, for example a compound of any of formulas I-IV, in the manufacture of a medicament for treatment of a bacterial infection in a mammal in need thereof.

In additional aspects, provided are pharmaceutical compositions comprising a therapeutically effective amount of a compound described herein, for example a compound of any of formulas I-IV, and a pharmaceutically acceptable carrier.

In another aspect, the compounds described herein, for example the compounds of formulas I-IV, can be used in combinations with other bioactive agents, such as anti-infective or anti-inflammatory agents. For example, to achieve an optimal therapeutic effect (such as a broad spectrum of action), compounds described herein, for example a compound of any of formulas I-IV, active against gram-positive pathogens may be co-administered in a combination with another antimicrobial agents active against gram-negative bacteria (e.g., quinolone, beta-lactam, aminoglycoside, colistin, a macrolide agent, a glycopeptide agent, daptomycin, etc.), an agent active against pathogenic fungi or yeast (e.g., allylamine, terbinafine, azole, etc.), or in combination with an antiviral agent (such as an entry-blocker, viral protease or DNA inhibitor, antiretroviral agent, etc.).

DETAILED DESCRIPTION OF THE INVENTION

Unless otherwise stated, the following terms used in the specification and Claims have the meanings given below.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. For example, $C_{1-20}$alkyl refers to alkyl or substituted alkyl of one to twenty carbon atoms, inclusive, including any straight and branched structures, such as methyl, ethyl, isopropyl, isobutyl, tert-butyl, neopentyl, benzyl, 4-methoxybenzyl, benzhydryl, and the like.

As used herein, R group labels in chemical structures and the description with the same number refer to the same R group, regardless of the formatting (super script, subscript, no format, etc.) of the number. For example, "R$^{\#}$" refers to the same R group as "R$_{\#}$" and "R#": R$^1$ refers to the same R group as "R$_1$" and "R1"; etc.

The terms "alkyl," "alkenyl," and "alkynyl" refer to both straight and branched groups, but reference to an individual radical such as "propyl" embraces only the straight chain radical, a branched chain isomer such as "isopropyl" being specifically referred to. The alkyl, alkenyl, etc., group may be optionally substituted with one, two, or three substituents selected from the group consisting of halo, aryl, Het$^1$, or Het$^2$. Representative examples include, but are not limited to, difluoromethyl, 2-fluoroethyl, trifluoroethyl, —CH=CH-aryl, —CH=CH—Het$^1$, —CH$_2$-phenyl, 2-trimethylsilylethyl, allyl, and the like.

The term "alkylidene" group means a divalent group formed by subtracting additional H at the terminal of an alkyl group. For example, ethylidene group —CH$_2$CH$_2$— is formed by subtracting H from ethyl group —CH$_2$CH$_3$, propylidene group —CH$_2$CH$_2$CH$_2$— is formed by subtracting H from propyl group —CH$_2$CH$_2$CH$_3$, and the like. The alkylidene group may be optionally substituted with one, two, or three substituents selected from the group consisting of C$_{1-12}$alkyl, halo, aryl, Het$^1$, and Het$^2$.

The term "cycloalkyl" means a cyclic saturated monovalent monocyclic or bicyclic hydrocarbon group of three to six carbon atoms, e.g., cyclopropyl, cyclohexyl, and the like. The cycloalkyl group may be optionally substituted with one, two, or three substituents selected from the group consisting of halo, aryl, Het$^1$, and Het$^2$.

The term "heteroalkyl" means an alkyl or cycloalkyl group, as defined above, having a substituent containing a heteroatom selected from halo, N, O, and S(O)$_n$, where n is an integer from 0 to 2, including, hydroxy (OH), C$_{1-4}$alkoxy, amino, thio (—SH), and the like. Representative substituents include —NR$_a$R$_b$, —OR$_a$, and —S(O)$_n$R$_c$, wherein R$_a$ is hydrogen, C$_{1-4}$alkyl, C$_{3-6}$cycloalkyl, optionally substituted aryl, optionally substituted heterocyclic, or —COR (where R is C$_{1-4}$alkyl); R$_b$ is hydrogen, C$_{1-4}$alkyl, —SO$_2$R (where R is C$_{1-4}$alkyl or C$_{1-4}$hydroxyalkyl), —SO$_2$NRR' (where R and R' are independently of each other hydrogen or C$_{1-4}$alkyl), —CONR'R" (where R' and R" are independently of each other hydrogen or C$_{1-4}$alkyl); n is an integer from 0 to 2; and R$_c$ is hydrogen, C$_{1-4}$alkyl, C$_{3-6}$cycloalkyl, optionally substituted aryl, or NR$_a$R$_b$ where R$_a$ and R$_b$ are as defined above. Representative examples include, but are not limited to, 2-methoxyethyl (—CH$_2$CH$_2$OCH$_3$), 2-hydroxyethyl (—CH$_2$CH$_2$OH), hydroxymethyl (—CH$_2$OH), 2-aminoethyl (—CH$_2$CH$_2$NH$_2$), 2-dimethylaminoethyl (—CH$_2$CH$_2$NHCH$_3$), benzyloxymethyl, thiophen-2-ylthiomethyl, and the like.

The term "halo" refers to fluoro (F), chloro (Cl), bromo (Br), or iodo (I).

The term "aryl" refers to phenyl, biphenyl, or naphthyl, optionally substituted with 1 to 3 substituents independently selected from halo, —C$_{1-4}$alkyl, —OH, —OC$_{1-4}$alkyl, —S(O)$_n$C$_{1-4}$alkyl wherein n is 0, 1, or 2, —C$_{1-4}$alkylNH$_2$, —NHC$_{1-4}$alkyl, —C(=O)H, or —C=N—OR$_d$ wherein R$_d$ is hydrogen or —C$_{1-4}$alkyl. Likewise, the term phenyl refers to the phenyl group optionally substituted as above.

The term "heterocyclic ring" refers to a monocyclic or bicyclic, aromatic ring (i.e., heteroaryl) or a saturated or unsaturated ring that is not aromatic where the ring contains 3 to 10 carbon atoms and 1 to 4 heteroatoms selected from the group consisting of oxygen, nitrogen, and S(O)$_n$ within the ring, where n is defined above. The heterocyclic ring may be optionally substituted with 1-3 groups selected from oxo, aryl, halo, CN, —C$_{1-4}$alkyl, —OH, —OC$_{1-4}$ alkyl, —S(O)$_n$C$_{1-4}$alkyl wherein n is 0, 1, or 2, —C$_{1-4}$alkylNH$_2$, —NHC$_{1-4}$alkyl, —C(=O)H, and —C=N—OR$_d$ wherein R$_d$ is hydrogen or C$_{1-4}$alkyl.

Examples of heterocyclic rings include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiadiazoletetrazole, thiazolidine, thiophene, benzo[b]thiophene, morpholinyl (or morpholino), thiomorpholinyl (also referred to as thiamorpholinyl), piperidinyl, pyrrolidine, tetrahydrofuranyl, 1,3-benzoxazine, 1,4-oxazine-3-one, 1,3-benzoxazine-4-one, pyrrolidine, pyrrolidine-2-one, oxazolidine-2-one, azepine, perhydroazepine, perhydroazepine-2-one, perhydro-1,4-oxazepine, perhydro-1,4-oxazepine-2-one, perhydro-1,4-oxazepine-3-one, perhydro-1,3-oxazepine-2-one, 2,3-dihydropyridin-4(1H)-one, and the like. Heterocyclic rings include unsubstituted and substituted rings.

Specifically, Het$^1$ (same as het$^1$, Het$_1$ or het$_1$) refers to a C-linked five- (5) or six-(6) membered heterocyclic ring, including bicyclic rings. Representative examples of "Het$^1$" include, but are not limited to, morpholinyl (or morpholino), pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone, or 3-azabicyclo[3.1.0]hexan-6-yl. Het$^1$ may be optionally substituted with 1-3 groups selected from oxo, aryl, halo, CN, —C$_{1-4}$alkyl, —OH, —OC$_{1-4}$ alkyl, —S(O)$_n$C$_{1-4}$alkyl wherein n is 0, 1, or 2, —C$_{1-4}$alkylNH$_2$, —NHC$_{1-4}$alkyl, —C(=O)H, and —C=N—OR$_d$ wherein R$_d$ is hydrogen or C$_{1-4}$alkyl.

Het$^2$ (same as het$^2$, Het$_2$, or het$_2$) refers to an N-linked five- (5) or six- (6) membered heterocyclic ring having 1 to 4 nitrogen atoms, and optionally having one oxygen or sulfur atom, including bicyclic rings. Representative examples of "Het$^2$" include, but are not limited to morpholinyl (or morpholino), pyrrolyl, imidazolyl, pyrazolyl, 1,2,3-triazolyl, 1,2,4-triazolyl, 1,2,3,4-tetrazolyl, isoxazolyl, 3-azabicyclo[3.1.0]hexan-3-yl, 1,3,9,9a -tetrahydrooxazolo[3,4-a]indol-1-yl, 2-alkylpyrrolo[3,4-c]pyrazol-5(2H,4H,6H)-yl, and 5H -pyrrolo[3,4-b]pyridin-6(7H)-yl, (2,3-dihydropyridin-4(1H)-one)-1-yl, and the like. Het$^2$ may be optionally substituted with 1-3 groups selected from oxo, aryl, halo, CN, —$C_{1-4}$alkyl, —OH, —$OC_{1-4}$ alkyl, —$S(O)_nC_{1-4}$alkyl wherein n is 0, 1, or 2, —$C_{1-4}$alkylNH$_2$, —NHC$_{1-4}$alkyl, —C(=O)H, and —C=N—OR$_d$ wherein R$_d$ is hydrogen or C$_{1-4}$alkyl.

"Hydroxyalkyl" means an alkyl radical, as defined herein, substituted with at least one, for example one, two, or three, hydroxy group(s), provided that if two hydroxy groups are present they are not both on the same carbon atom. In one embodiment, examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, 2-hydroxyethyl, 2,3-dihydroxypropyl, or 1-(hydroxymethyl)-2-hydroxyethyl, and the like.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and Claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A hydrogen (H) or carbon (C) substitution for compounds of the formula I include a substitution with any isotope of the respective atom. Thus, a hydrogen (H) substitution includes a $^1$H, $^2$H (deuterium), or $^3$H (tritium) isotope substitution, as may be desired, for example, for a specific therapeutic or diagnostic therapy, or metabolic study application. Optionally, a compound of this invention may incorporate a known in the art radioactive isotope or radioisotope, such as $^3$H, $^{15}$O, $^{12}$C, or $^{13}$N isotope, to afford a respective radiolabeled compound of formula I.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and Claims includes both one and more than one such carrier.

A "pharmaceutically acceptable salt" of a compound means a salt that is pharmaceutically acceptable and that possesses the desired pharmacological activity of the parent compound. Such salts include:

(1) Salts formed when an acidic proton present in the parent compound either is replaced by a suitable metal ion, e.g., an alkali metal ion; or coordinates with ammonia or an organic base such as natural or unnatural amino acid, L-lysine, L-arginine, L-serine, L-glutamine, ethanolamine, diethanolamine, triethanolamine, tromethamine, an aminosugar, N-methylglucamine (meglumine), and the like. Said salt form may be either mono-basic salt, such as a salt formed with a single acidic group, or a di-basic salt, such as salt formed with two acidic groups present, as may be required. The salt may contain an excess of an inorganic or organic base over a stoichiometric amount calculated per number of acidic groups present in a compound of this invention, as may be required, for example, for solution pH adjustment or enhanced storage stability of said salt; or (2) Acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, mandelic acid, methanesulfonic acid, trifluoromethanesulfonic acid, ethanesulfonic acid, 1,2-ethanedisulfonic acid, 2-hydroxyethanesulfonic acid, benzenesulfonic acid, salicylic acid, stearic acid, muconic acid, and the like.

"Treating" or "treatment" of a disease includes inhibiting the disease, i.e., arresting or reducing the development of the disease or its clinical symptoms. This is achieved, for example, by inhibiting the bacterial growth, or by killing of bacterial cells present at the infection site, such as an organ tissue, or blood.

"Treating" or "treatment" may also include preventing the disease, i.e. causing the clinical symptoms of the disease not to develop in a mammal that may be exposed to or predisposed to the disease but does not yet experience or display symptoms of the disease. For example, the treatment with antibacterial agents is often used before intra-abdominal surgery, to prevent an onset of possible infection after the medical procedure.

"Treating" or "treatment" may additionally include relieving the disease, i.e., causing regression of the disease or its clinical symptoms. For example, some antibacterial agents, in addition to the direct inhibition of microbes, may additionally inhibit toxins already produced by bacterial pathogens, and thus relieve a toxic shock syndrome and/or inflammation in a subject under the treatment.

"Therapeutic agent" or "therapeutic compound" means a bioactive agent or drug which, when administered to a mammal in need thereof, can prevent, relieve, or eliminate a disease or disease symptom(s), such as infection, malignant growth, inflammation, pain, elevated blood pressure, etc.

A "therapeutically effective amount" means the amount of a compound that, when administered to a mammal for treating a disease, is sufficient to effect such treatment for the disease. The therapeutically effective amount will vary depending on the compound, the disease and its severity and the age, weight, etc., of the mammal to be treated. Therapeutically effective amount may also be referred to as any amount of a compound that is sufficient to achieve the desired beneficial effect, including preventing the disease, inhibiting the disease, or relieving the disease, as described above in (1)-(3). For example, the amount of a compound can range between 0.1-250 mg/kg, or preferably, 0.5-100 mg/kg, or more preferably, 1-50 mg/kg, or even more preferably, 2-20 mg/kg. More preferably, said amount of a compound is administered to a mammal once-daily. Even more preferably, said amount of a compound is administered to a mammal once-weekly or once-biweekly.

"Leaving group" has the meaning conventionally associated with it in synthetic organic chemistry, i.e., an atom or group capable of being displaced by a nucleophile and includes halogen, $C_{1-4}$alkylsulfonyloxy, ester, or amino such as chloro, bromo, iodo, mesyloxy, tosyloxy, trifluorosulfonyloxy, methoxy, N,O-dimethylhydroxyl-amino, and the like.

"Prodrug" means any compound which releases an active parent drug according to a compound of the subject invention in vivo when such prodrug is administered to a mammalian subject. Various prodrugs have been described, for example, in the following publications: Alexander et al. J. Med. Chem. 1988, p. 318; Alexander et al. J. Med. Chem., 1991, p. 78; Murdock et al. J. Med. Chem., 1993, p. 2098; Davidsen et al. J. Med. Chem., 1994, p. 4423; Robinson et al. J. Med. Chem., 1996, p. 10; Keyes et al. J. Med. Chem., 1996, p. 508; Krise et al. J. Med. Chem., 1999, p. 3094; Rahmathullah et al. J. Med. Chem., 1999, p. 3994; Zhu et al. Bioorg. Med. Chem. Lett., 2000, p. 1121; Sun et al., J. Med. Chem., 2001, p. 2671; Ochwada et al., Bioorg. Med. Chem. Lett., 2003, p. 191; Sohma et al. Med. Chem., 2003, p. 4124; Ettmayer et al. J. Med. Chem., 2004, p. 2393; Stella et al., Adv. Drug Delivery Rev., 2007, p. 677, Josyula et al. International Patent Publication No. WO 2005/028473; Rhee et al. International Patent Publication No. WO 2005/058886, and EP 1,683,803. Following methods of these publications and refs. cited therein, respective prodrugs of the compounds of the present invention can be likewise prepared. Thus, prodrugs of compounds of the formulas I-III herein are prepared by modifying functional groups present in a compound of the subject invention in such a way that the modifications may be cleaved in vivo to release the parent compound. Said prodrugs can be used, for example, to improve aq. solubility, oral, transdermal, or ocular bioavailability, to achieve a controlled (e.g., extended) release of the drug moiety, to improve tolerability, etc. Prodrugs include compounds of the subject invention wherein a hydroxy, sulfhydryl, amido or amino group in the compound is bonded to any group that may be cleaved in vivo to regenerate the free hydroxyl, amido, amino, or sulfhydryl group, respectively. Examples of prodrugs include, but are not limited to esters (e.g., acetate, formate, benzoate, phosphate or phosphonate derivatives), carbamates (e.g., N,N-dimethylaminocarbonyl), N-phosphoramides, phosphoramidates, of hydroxyl or amine-derived functional groups in compounds of the subject invention. Prodrug derivative can be used either as a neutral prodrug form (e.g. acid or amine), or a respective salt form thereof [e.g. sodium salt of a phosphate prodrug, or an amine salt (e.g. hydrochloride, citrate, etc.) for an amine group-bearing prodrug], or a zwitterionic form if both positively and negatively charged/ionizable functions are present.

The term "mammal" refers to all mammals including humans, livestock, and companion animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "r.t." for room temperature).

Illustrative Aspects

Within the broadest definition of the present invention, certain compounds of the compounds of formula I may be preferred. Specific and preferred values listed below for radicals, substituents, and ranges, are for illustration only; they do not exclude other defined values or other values within defined ranges for the radicals and substituents.

In some compounds of the present invention $C_{1-20}$alkyl can be methyl, ethyl, propyl, isopropyl, butyl, iso-butyl, sec-butyl, tert-butyl, and isomeric forms thereof.

In some compounds of the present invention $C_{2-4}$alkenyl can be vinyl, propenyl, allyl, butenyl, and isomeric forms thereof (including cis and trans isomers).

In some compounds of the present invention $C_{3-6}$cycloalkyl can be cyclopropyl, cyclobutyl, cyclopentyl, cyclohexyl, and isomeric forms thereof.

In some compounds of the present invention $C_{1-20}$heteroalkyl can be hydroxymethyl, hydroxyethyl, and 2-methoxyethyl.

In some compounds of the present invention halo can be fluoro (F) or chloro (Cl).

In some compounds of the present invention $R^2$ can be 5-$R^7$-isoxazol-3-yl, wherein $R^7$ is H, $C_{1-3}$alkyl, halo, or CN.

In some aspects, groups $R^1$, $R^2$, $R^3$, and $R^4$ are independently selected from H or F.

In some aspects, group $R^1$ is F, $R^2$ and $R^6$ are both H.

In some aspects, $R^2$, $R^3$ and $R^4$ independently can be H or F.

In some aspects, one of $R^4$ and $R^5$ is H and the other is F.

In some aspects, $Het^1$ can be 2-pyridyl, 3-pyridyl, 4-pyridyl, 3-isoxazolyl, 4-isoxazolyl, 5-isoxazolyl, 1,2,3-triazol-1-yl, 1,2,5-thiadiazol-3-yl, and isoxazolidin-3-yl group.

In some aspects, $Het^2$ can be pyrrolyl, imidazolyl, pyrazolyl, 1,2,3-triazolyl, 1,2,4-triazolyl, 1,2,3,4-tetrazolyl, 2,3-dihydropyridin-4(1H)-one-1-yl, and isoxazolidin-3-yl group.

It will also be appreciated by those skilled in the art that compounds of the present invention may have additional chiral centers and be isolated in optically active and racemic forms. The present invention encompasses any racemic, optically active, tautomeric, or stereoisomeric form, or mixture thereof, of a compound of the invention.

One group of compounds of the present invention is illustrated below:

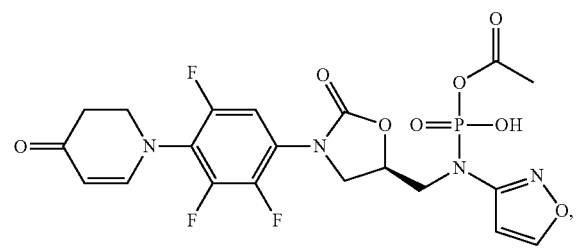

-continued
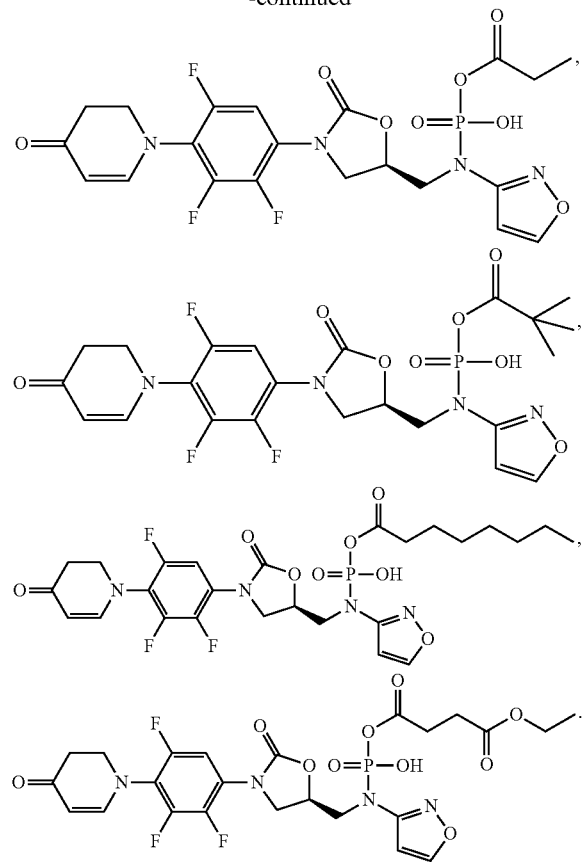
Another group of compounds of the present invention is illustrated below:
-continued
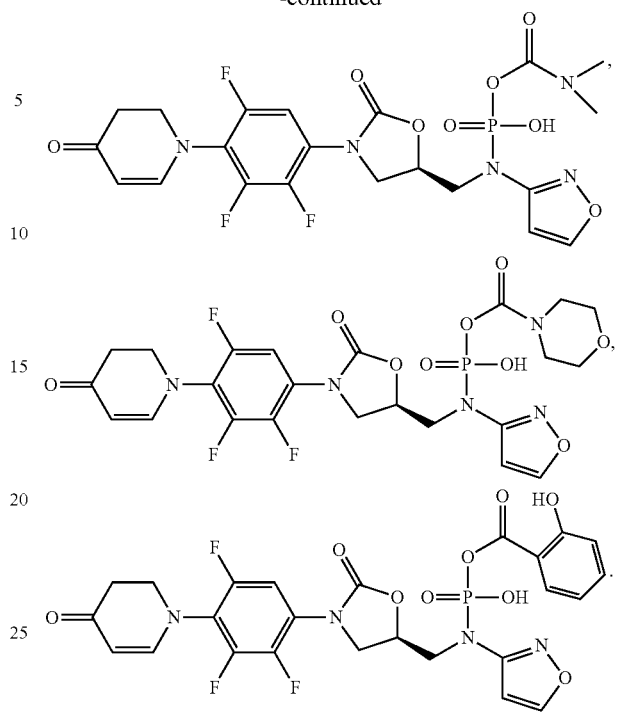
Another group of compounds of the present invention is illustrated below:
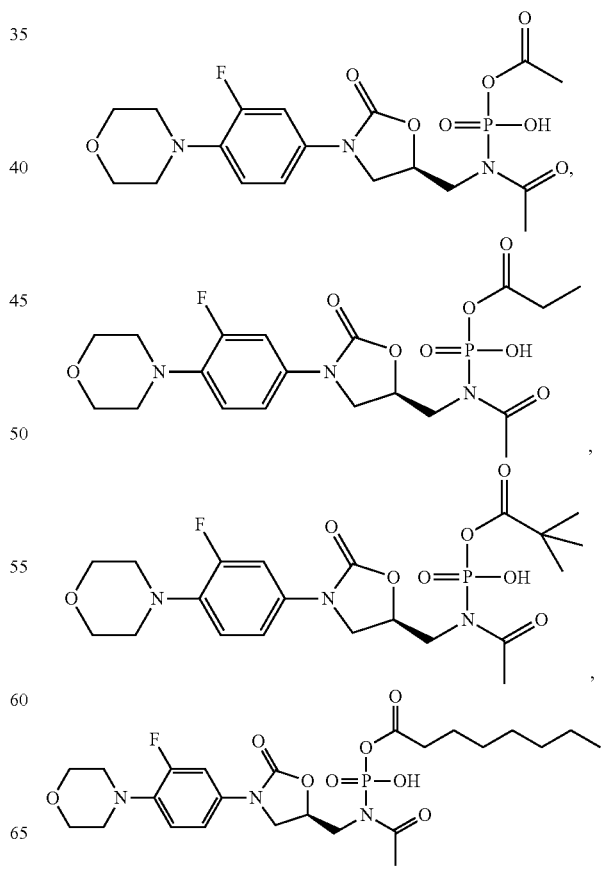
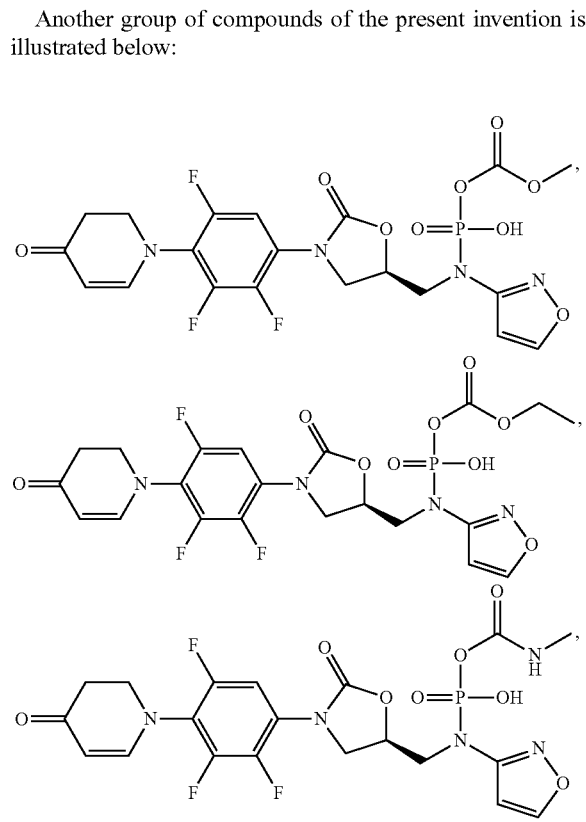

-continued
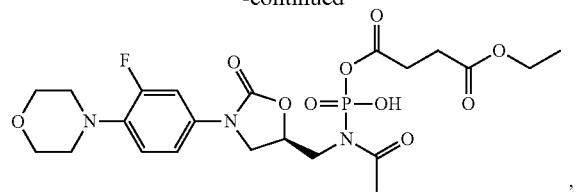
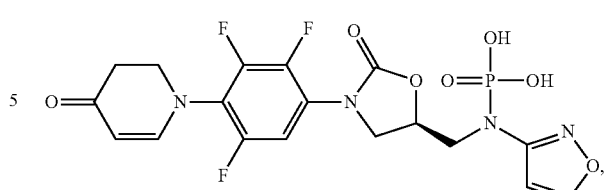
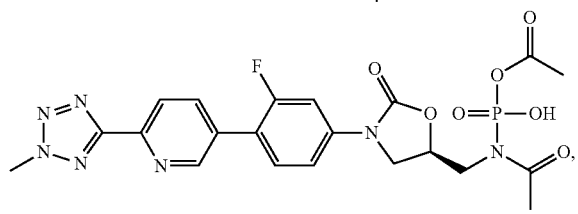
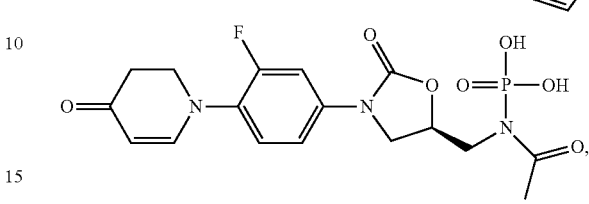
Another group of prodrugs and intermediates of the present invention is illustrated below:
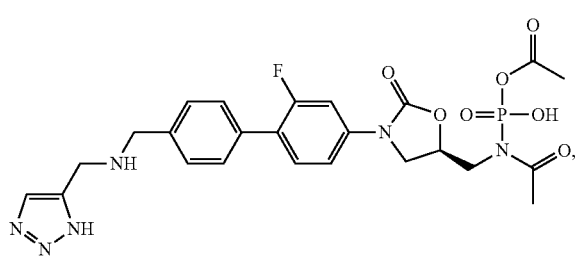
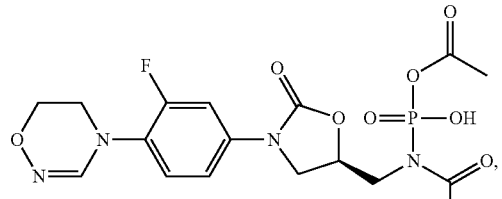
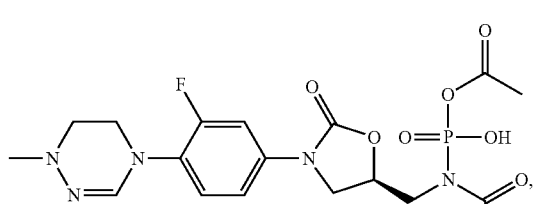
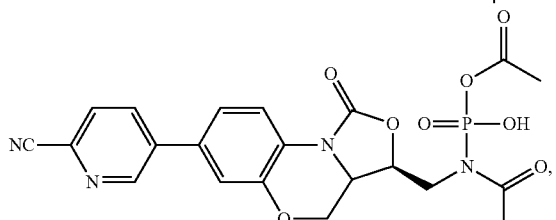
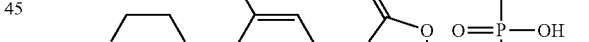
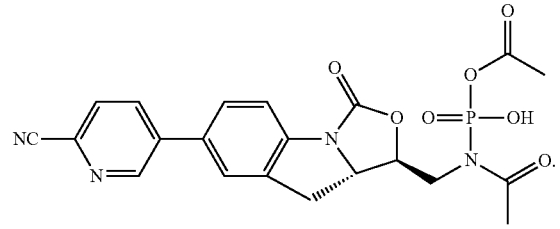
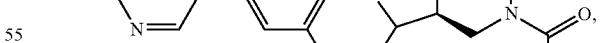
An additional group of prodrugs and intermediates of the present invention is illustrated below:
Additional group of compounds of the present invention is illustrated below:

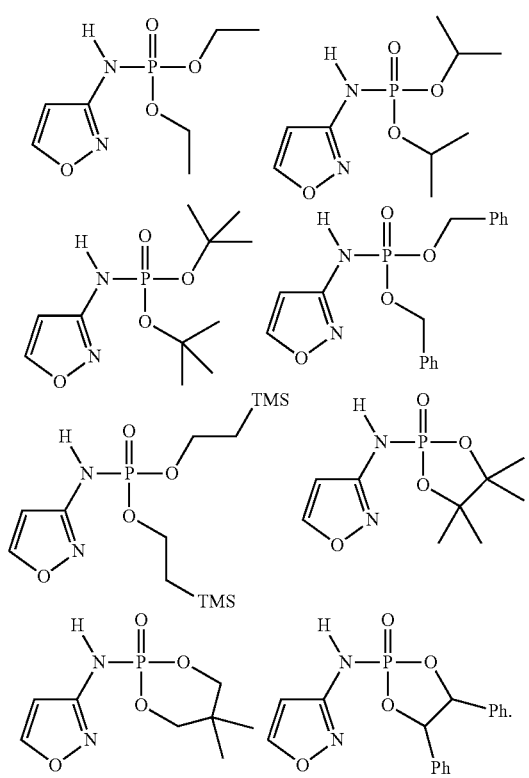

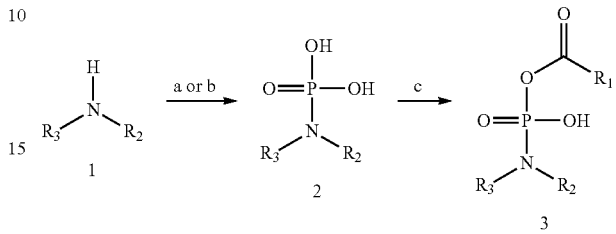

General Synthetic Methods

The compounds of this invention can be prepared in accordance with one or more of Schemes discussed below. Synthesis of phosphoramidate and O-carbonyl phosphoramidate compounds of this invention may generally follow some known in the synthetic art methods described for certain non-phosphoramidate derivatives incorporating NH-containing groups, such as (isoxazol-3-yl)amino or NH-amide groups, described, for example, in PCT publications WO 2000/021960, WO 2004/056816, WO 2006/043121, and WO 2009/020616.

Some general approaches to the compounds of this invention are illustrated in general Scheme 1.

Scheme 1. General synthesis of O-carbonyl phosphoramidates.

a) POCl₃; base: e.g., N-methylmorpholine (NMM), TEA, Py or DIEA; then water; b) (t-BuO)₂PN(i-Pr)₂, 1H-tetrazole, t-BuOOH; then TFA or HCl; c) base: e.g. Na₂CO₃, NaOAc, Na₂HPO₄, TEA, NMM, (dimethylamino)methyl-polystyrene, or alike;
[R¹C(=O)₂]O, Alkyl-N=C=O, or R¹C(=O)X,
wherein X = Cl, 4-nitrophenoxy, pentafluorophenoxy, or alike.

To achieve the requisite phosphoramidate derivatization, the N-protected (isoxazole-3-yl)amine (such as N-Boc-protected 3-(tert-butoxycarbonyl)aminoisoxazole described in the PCT WO 2000/021960) can be intentionally replaced for a protected phosphoramidate reagent (such as O,O-dialkyl isoxazol-3-ylphosphoramidate, or O,O -dialkylacetylphosphoramidate). Subsequent deprotection of the resulted protected phosphoramidate oxazolidinone followed by acylation to introduce the requisite O-carbonyl group affords the target compounds of this invention. Optionally, compounds of this invention are isolated in a salt form, such as an alkali metal salt, or an amine salt.

Additional general methods of Scheme 2 illustrate the synthesis of O-carbonyl phosphoramidate prodrugs of antibacterial oxazolidinones.

Scheme 2. General synthesis of O-carbonyl phosphoramidate oxazolidinone derivatives.

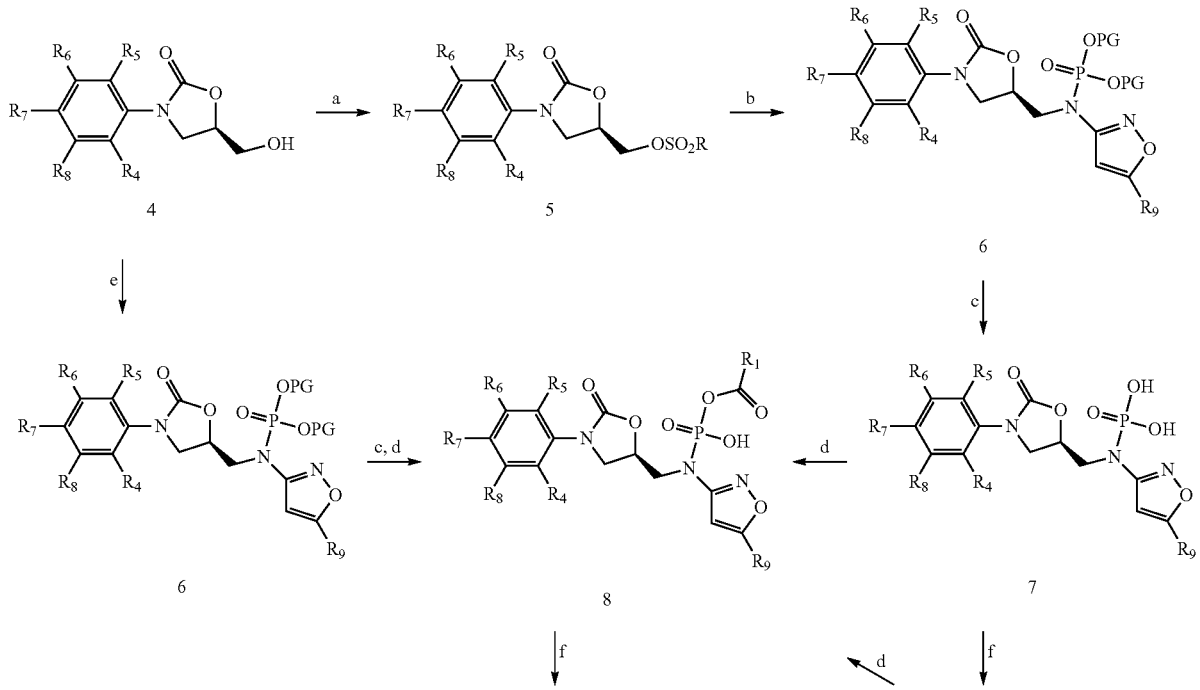

-continued

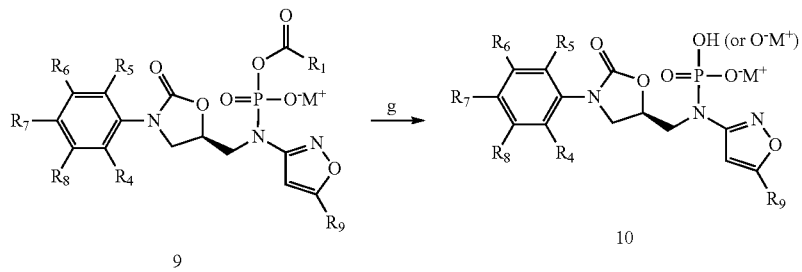

a) RSO₂Cl or (RSO₂)₂O; base: e.g., N-methylmorpholine (NMM), TEA, Py, or DIEA; b) O,O-dialkyl- or O,O-dicycloalky-lisoxazol-3-ylphosphoramidate reagent; base: e.g. NaH, LiOBu-t, KOBu-t, tetramethylguanidine, or alike; c) deprotecting agent: e.g. TMSBr or TMSI for PG = i-Pr or i-Bu, H₂/Pd/C for PG = Bn; TFA, MsOH, or HCl for PG = t-Bu, or PG = p-methoxybenzyl, or PG = benzhydryl; KF, TBAF, or HF for PG = TMSCH₂CH₂; ammonia or LiOH for PG = NCCH₂CH₂; d) base: e.g. Na₂CO₃, NaOAc, Na₂HPO₄, TEA, NMM, (dimethylamino)methyl-polystyrene, or alike; [R¹C(═O)₂]O, Alkyl-N═C═O, or R¹C(═O)X, wherein X = Cl, 4-nitrophenoxy, pentafluorophenyl, or alike; e) Mitsunobu reagents: e.g., Ph₃P/i-PrO₂CN═NCO₂Pr—I (DIAD); Ph₃P/H₂NC(═O)N═NC(═O)NH₂; Bu₃P/DIAD; Ph₂P-Polystyrene/DIAD; or alike; f) alkali metal base or amine, e.g. NaOH, Na₂CO₃, NaHCO₃, NaOAc, Na₂HPO₄, meglumine, glycine, lysine, or alike; g) alkali metal base or amine, NaOH, Na₂CO₃, NaHCO₃, NaOAc, Na₂HPO₄, meglumine, glycine, lysine, or alike; protic solvent, such as water-containing EtOH, MeCN, THF, or an alcohol, such as EtOH.

As illustrated in Scheme 2, O-carbonyl phosphoramidate compounds of this invention (e.g., compounds 8 or 9) may be optionally de-carbonylated (e.g., O-deacetylated) an alkali metal or amine salts of the latter into respective phosphoramidate compounds 10 in the Scheme 2, which are also useful as prodrugs. As may be preferred for specific use, the compounds 10 may be prepared as mono-basic salts (when using 1 equivalents of an alkali metal or amine base), or di-basic salts (when using at least 2 equivalents of an alkali metal or amine base, or of any combination of these reagents). In turn, the compounds 10 may be converted into O-carbonyl phosphoramidate compounds by O-carbonylation (e.g., O-acylation) of compounds 10. This allows for facile variations in different R¹ groups (when using different acylating reagents), as may be needed to prepare a specific compound of this invention.

A multitude of alcohol and alkyl- and arylsulfonate oxazolidinone derivatives of types 1 and 2 employed in Scheme 2 have been described in the prior art, such as PCT publications WO 2000/021960, WO 2004/056816, WO 2006/043121, and WO 2009/020616.

O,O-Dialkyl or O,O-dicycloalkyl (isoxazol-3-yl)phosphoramidate compounds used for preparation of compounds provided herein (for example, in step (b) of Scheme 2) can be prepared as illustrated in Scheme 3 below.

Scheme 3. General synthesis of (isoxazol-3-yl)phosphoramidate compounds.

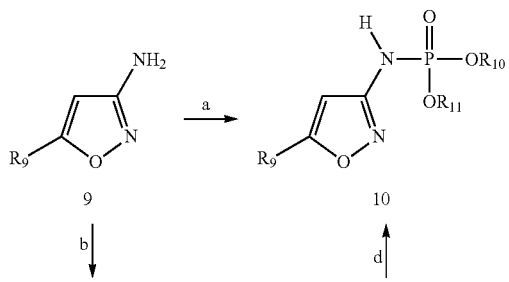

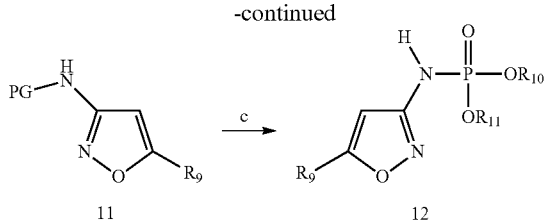

a) (R¹⁰O)(R¹¹O)P(═O)Cl₂; base: Py, NMM, DIEA, or the like; b) protection with a protective group (PG) aided with an optional base: Py, NMM, DIEA, DMAP, or the like; acylating or sulfonylating reagent: ArSO₂Cl for PG = ArSO₂; Boc₂O for PG = Boc; CbzCl or CbzOSu for PG = Cbz; and the like; c) (R¹⁰O)(R¹¹O)P(═O)Cl₂; base: DBU, DMAP, Py, NMM, KOBu-t, LiOBu-t, and the like; d) deprotecting reagent: MsOH or MsOH—TFA for PG = ArSO₂; RSH, base (Na₂CO₃, DBU, NMM, and the like) for PG = nosylate; TFA for PG = Boc; H₂/Pd/C or HCOONH₄/Pd for PG = Cbz; and the like.

Phosphorylation methods generally related to those of Scheme 3 have been described, for example, in publications Zhurnal Obshchei Khimii. 1990, vol. 60, p. 1991, and PCT WO 9735864 that denote preparation of certain isoxazol-3-ylphosphoramidates, but limited to diphenyl isoxazol-3-ylphosphoramidates. Importantly, these diphenyl derivatives are not suitable for a facile phosphoramidate O-deprotection, which is required to prepare the compounds of this invention.

In contrast, the new O,O-dialkyl and O,O-dicycloalkyl (isoxazol-3-yl)phosphoramidates provided herein allow for this critical deprotection step in the preparation of O-carbonyl (isoxazol-3-yl)phosphoramidateoxazolidinones. No other than O,O-diphenylphosphoramidates derived from 3-aminoisoxazoles have been previously described, and no specific compounds or phosphorylated intermediates of this invention provided.

Optionally, methods of Schemes 1 and 2 may include additional treatment of intermediates 2, 6, and 7, and of the final products 3 and 8 to remove residual deprotecting agents and/or by-products. For example, silver reagents such as silver salts immobilized on a suitable support (e.g., Ag₂CO₃-active carbon, or a silver sulfonate resins) may be used to remove traces of iodides, while ion-exchange resins (e.g., quarternary ammonium polystyrene resins) or amine resins (e.g., aminomethyl polystyrene, methylaminomethyl polystyrene, or dimethylaminomethyl polystyrene) may be used to remove excessive acid impurity, if needed. Likewise, acidic ion-exchange resins (such as sulfonic acid or carboxylic acid polystyrene resins) may be optionally employed to remove inorganic salts and/or convert the products from salt form into acidic form. Similar purification reagents have been described, for example, in the PCT publication WO 2010/121021, and in the U.S. Pat. No. 7,588,690.

Additional detailed synthetic schemes for the syntheses of specific compounds of the present invention are illustrated by methods described for Examples below.

EXAMPLES

Embodiments of the present invention are described in the following examples, which are meant to illustrate and not limit the scope of this invention. Common abbreviations well known to those with ordinary skills in the synthetic art used throughout. 400 MHz $^1$H NMR spectra ($\delta$, ppm) are recorded in DMSO-$d_6$ unless specified otherwise. Mass-spectroscopy (MS) data (m/z) for a positive ionization method are provided. Chromatography means silica gel chromatography unless specified otherwise. TLC means thin-layer chromatography. HPLC means high-performance liquid chromatography. Common abbreviations such as DMSO (dimethylsulfoxide), DCM (dichloromethane), THF (tetrahydrofuran), MTBE (methyl tert-butyl ether), DMF (N,N-dimethylformamide) are used throughout. Unless specified otherwise, all reagents were either from commercial sources, or made by conventional methods described in available literature.

Example 1

Compound of Structure

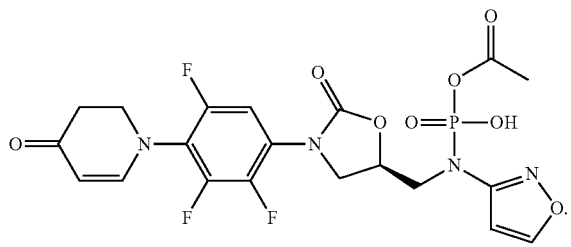 [SMILES: CC(=O)OP(=O)(O)N(C[C@H]1CN(c2cc(F)c(N3C=CC(=O)CC3)c(F)c2F)C(=O)O1)c1ccon1]

Method A. Scheme for the Compound of Example 1, Method A:

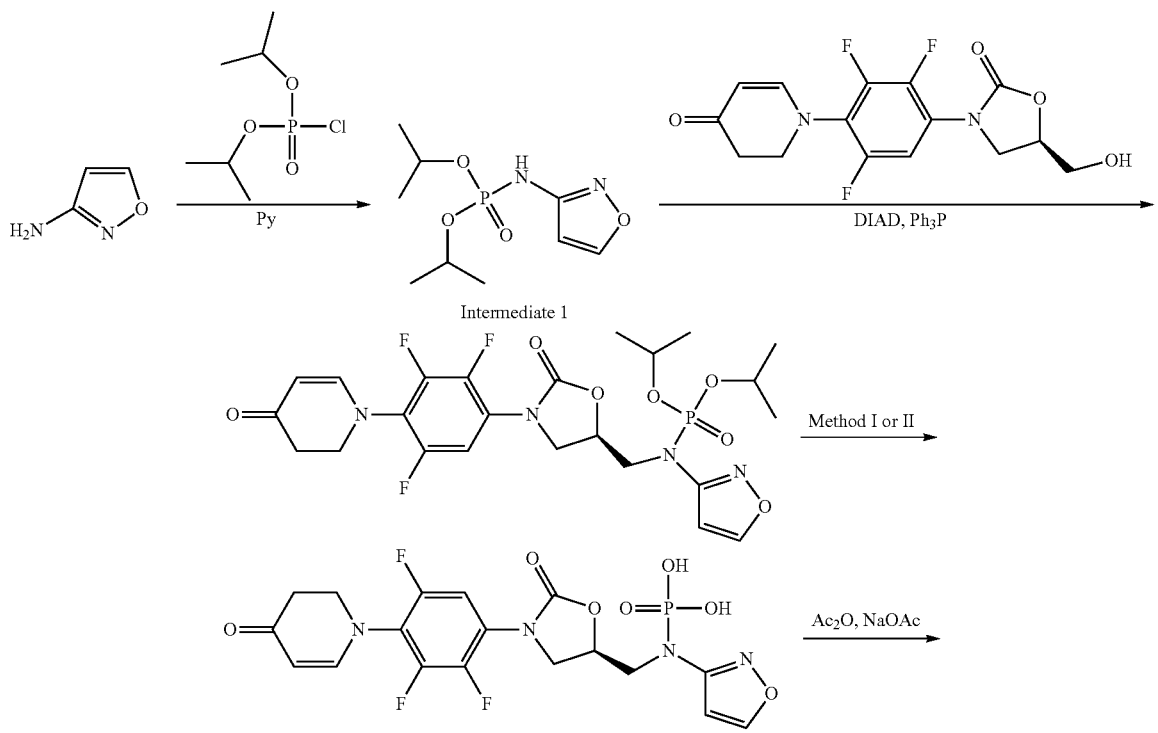

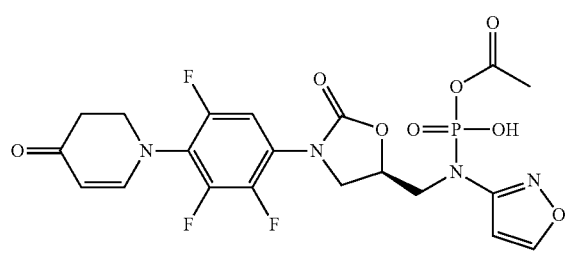

Example 1

Intermediate 1. Diisopropylchlorophosphate (706 μL) was added dropwise with stirring to 3-aminoisoxazole (0.37 mL) in pyridine (Py, 5 mL) under nitrogen at ca. −5 to 0° C., and the mixture was stirred and allowed to warm up to r.t., then stirred o.n. Volatiles were removed under vacuum, and the residue was taken into EtOAc-MTBE 1:1 (ca. 50 mL) and 5% aq. citric acid (ca. 25 mL). Organic layer was washed with 5% aq. citric acid (25 mL), sat. aq. NaHCO₃ (2×25 mL), brine (25 mL), and dried (MgSO₄) with addition of active carbon (ca. 2 cc). Solvent was removed under vacuum and the semi-crystalline residue was triturated with MTBE-hexanes ca. 1:3. The crystalline product was filtered off and dried under vacuum. ¹H NMR: 8.18 (s, 1H), 6.35 (d, J 1.2 Hz, 1H), 6.18 (br. d, J 7.8 Hz, 1H), 4.74 (m, 2H), 1.40 (d, J 6.0 Hz, 6H), 1.31 (d, J 6.3 Hz, 6H). MS: 249 [M+H].

Intermediate 2. DIAD (76 μL) was added to a mixture of Intermediate 1 (112 mg), (R)-5-(hydroxymethyl)-3-(2,3,5-trifluoro-4-(4-oxo-3,4-dihydropyridin-1(2H) -yl)phenyl)oxazolidin-2-one (103 mg; prepared as described in the PCT WO 2009/020616), and Ph₃P (118 mg) in THF (3 mL) under nitrogen at r.t, and the solution was stirred at r.t. o.n. Solvent was removed under vacuum, and the product was purified by silica gel chromatography (hexanes-EtOAc 4:1, then hexanes-EtOAc 1:1). Combined product fractions were evaporated, and the product was dried under vacuum. Glassy colorless material. ¹H NMR (CDCl₃): 8.21 (d, J 1.6 Hz, 1H), 7.46 (m, 1H), 7.07 (d, J 7.6 Hz, 1H), 6.42 (d, J 1.6 Hz, 1H), 5.29 (d, J 7.6 Hz, 1H), 5.23 (m, 1H), 4.82 (m, 1H), 4.68 (m, 1H), 4.32-4.19 (m, 2H), 4.01 (m, 1H), 3.91 (m, 3H), 2.69 (m, 2H), 1.40 (t, J 6.0 Hz, 6H), 1.27 (m, 6H).MS: 573 [M+H].

Intermediate 3, Method I. Iodotrimethylsilane (TMSI, 26 uL) was added with stirring to Intermediate 2 (15 mg) in DCM (300 μL) under nitrogen, and the solution was stirred at r.t. o.n. Volatiles were removed under vacuum, and the resulted product was washed with MTBE and then dried under vacuum. ¹H NMR (DMSO-d₆): 8.67 (d, J 1.6 Hz, 1H), 7.60 (m, 1H), 7.53 (d, J 8.0 Hz, 1H), 6.54 (d, J 1.6 Hz, 1H), 5.10 (d, J 8.0 Hz, 1H), 5.06 (m, 1H), 4.21 (m, 1H), 4.02 (m, 1H), 3.92 (m, 4H), 2.53 (m, 2H; overlaps with DMSO-d₆). MS: 489 [M+H]. Optionally, this compound was isolated as a sodium salt by dissolution in about 0.2M aqueous Na₂CO₃ (to media pH of about 8.5), EtOAc wash, and lyophilization of the aqueous layer. ¹H NMR for the sodium salt of Intermediate 3 (in D₂O): 8.11 (d, J 2.0 Hz, 1H), 7.44 (d, J 7.6 Hz, 1H), 7.25 (m, 1H), 6.52 (d, J 2.0 Hz, 1H), 5.19 (d, J 7.6 Hz, 1H), 5.09 (m, 1H), 4.12 (m, 1H), 3.98 (m, 1H), 3.92-3.82 (m, 4H), 2.62 (m, 2H).

Intermediate 3, Method II. Bromotrimethylsilane (TMSBr, 66 μL) was added dropwise with stirring to Intermediate 2 (64 mg) in CHCl₃ (0.4 mL) under nitrogen, and the mixture was stirred for at 40-50° C.o.n. Volatiles were removed under vacuum, the residue was triturated and washed with excess of methyl t-butyl ether (MTBE), then dried under vacuum. MS: 489 [M+H].

Compound of Example 1. NaOAc (2.14 g) was added portionwise with stirring to the crude Intermediate 3 (ca. 0.9 mmol; prepared as described above in Method A) in DMSO-MeCN 1:10 (11.0 mL), followed by Ac₂O (355 mg). The mixture was stirred for 1 h, then MTBE (ca. 60) was added. Precipitated solids were filtered off, and stirred with 5% EtOH in DCM (100 mL) for 20 min. The suspension was filtered aiding with an excess of EtOAc. Volatiles were evaporated and the residual was triturated and washed with EtOAc-MTBE 3:1 (4 mL). The product was filtered off and dried under vacuum to afford the compound of Example 1 as its sodium salt, an off-white solid. ¹H NMR: 8.43 (d, J 1.6 Hz, 1H), 7.64 (m, 1H), 7.50 (d, J 7.6 Hz, 1H), 6.72 (d, J 1.6 Hz, 1H), 5.06 (d, J 7.6 Hz, 1H), 5.02 (m, 1H), 4.18-4.12 (m, 2H), 3.93-3.82 (m, 4H), 2.51 (m, 2H), 1.95 (s, 3H). MS: 531 [M+H].

Method B. Scheme for the compound of Example 1, Method B:

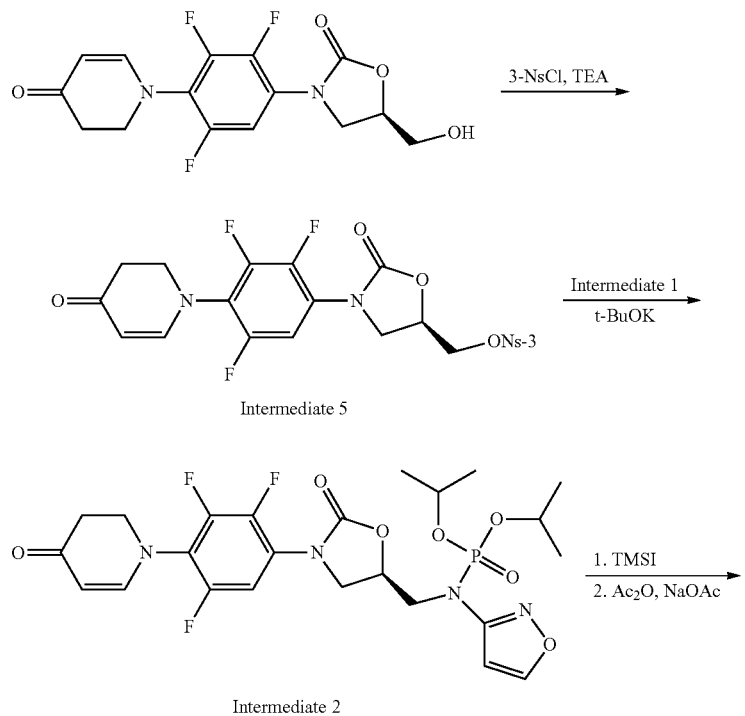

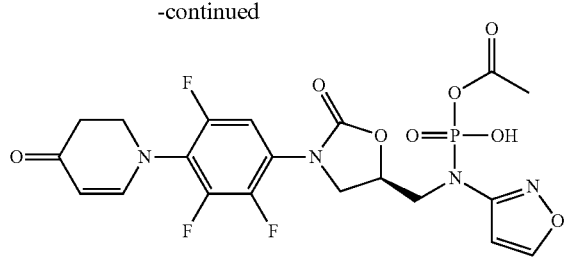

Example 1

Intermediate 5. 3-Nitrobenzenesulfonyl chloride (NsCl, 16.0 g) was added portionwise with stirring to a solution R)-5-(hydroxymethyl)-3-(2,3,5-trifluoro-4-(4-oxo-3,4-dihydropyridin-1(2H)-yl)phenyl)oxazolidin-2-one (18.0 g; prepared as described in the PCT WO 2009/020616) and triethylamine (TEA, 8.4 g) in DCM (200 mL) at ca. 0-2° C. The mixture was stirred at this temperature for 2 h, then filtered. The filtrate washed with water, brine, and dried (MgSO$_4$). The solvent was evaporated and the product dried under vacuum. Yellow solid. $^1$H NMR: 8.62 (d, J 9.2 Hz, 1H), 8.56 (s, 1H), 8.37 (d, J 8.0 Hz, 1H), 7.99 (m, 1H), 7.49-7.44 (m, 2H), 5.06 (d, J 8.0 Hz, 1H), 4.99 (m, 1H), 4.52 (m, 2H), 4.13 (m, 1H), 3.86 (m, 2H), 3.75-3.73 (m, 1H), 2.49 (m, 2H). MS: 528 [M+H].

Compound of Example 1. t-BuOK (27.7 g) was added portionwise with stirring under nitrogen atmosphere to a solution of the Intermediate 1 (43.2 g) in 2-methyltetrahydrofuran (0.764 L) at 0-10° C. After about 1 h, the mixture was heated to 30-35° C., then Intermediate 5 (76.4 g) was added portionwise with stirring, and the mixture was stirred for additional 15-24 h (until the Intermediate 5 was consumed; optionally, this step is performed using about 0.2-0.3 L of DMF instead of 2-methyltetrahydrofuran). The mixture was cooled to 10-20° C., then EtOAc (0.35 L) and water (1.15 L) were added. Upon extraction, EtOAc layer was separated, and the aqueous layer was extracted with 2-methyltetrahydrofuran (0.9 L). Combined organic layers were washed with 5% Na$_2$SO$_4$ (2×0.99 L) and treated with active carbon for decoloration. The solvent was evaporated under vacuum and dried. The crude Intermediate 2 was re-dissolved in DCM, evaporated under vacuum, and the latter procedure was repeated. Resulted residue was dissolved in dry DCM (0.765 L). This solution was chilled to about −5-5° C. under nitrogen, and trimethylsilyl iodide (TMSI, 116 g) was added dropwise with stirring. The mixture was allowed to warm up to r.t. and stirred for additional 2-3 h. Most volatiles were then removed under vacuum. The residue was re-dissolved in DCM, evaporated under vacuum, and the latter procedure was repeated. Resulted residue was dissolved in MeCN (0.765 L) and cooled to about −5-5° C. NaOAc (95.1 g) was added portionwise with stirring, and the mixture was stirred for additional 0.5-1 h. Then Ac$_2$O (59.2 g) was added dropwise with stirring. The mixture was allowed to warm up to r.t and stirred for about 12-16 h. Then MTBE (3.1 L) was added, and the suspension was stirred for about 1 h. The solid was filtered off and rinsed with MTBE. Resulted crude product was purified by preparative HPLC(C18 column) using a gradient elution from water to MeCN. Combined fractions containing the product were lyophilized under vacuum to afford the compound of Example 1 as its sodium salt, an off-white solid. $^1$H NMR: 8.43 (d, J 1.6 Hz, 1H), 7.64 (m, 1H), 7.50 (d, J 7.6 Hz, 1H), 6.72 (d, J 1.6 Hz, 1H), 5.06 (d, J 7.6 Hz, 1H), 5.02 (m, 1H), 4.18-4.12 (m, 2H), 3.93-3.82 (m, 4H), 2.51 (m, 2H), 1.95 (s, 3H). MS: 531 [M+H]. Combustion analysis: C, 42.40%; H, 3.38%; N, 10.00%; calcd. for solvate (hydrate) C$_{20}$H$_{17}$F$_3$N$_4$NaO$_8$P.H$_2$O: C, 42.12; H, 3.36; N, 9.82.

Method C. Scheme for the compound of Example 1, Method C:

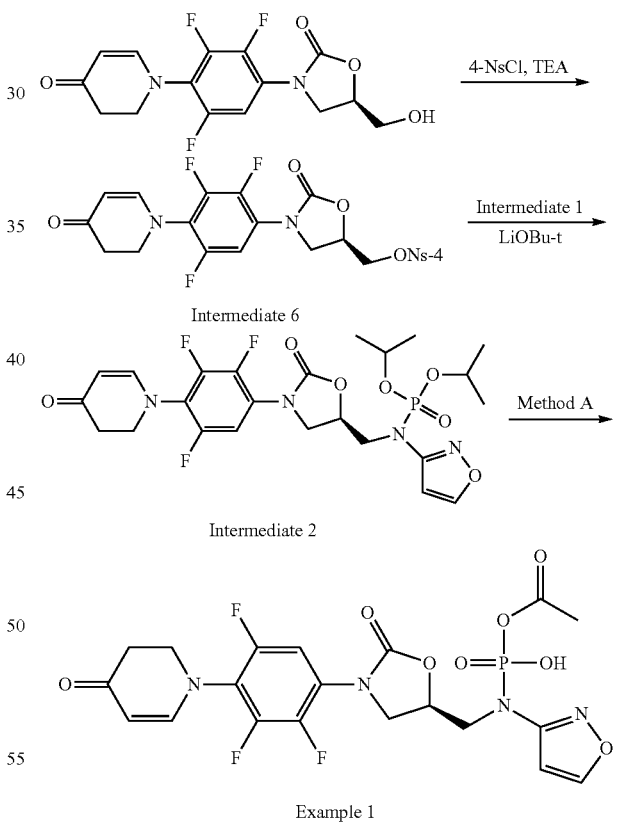

Example 1

Intermediate 6. The Intermediate 6 was prepared analogously to the procedure for preparation of Intermediate 5, except using 4-nitrobenzenesulfonyl chloride instead of 3-nitrobenzenesulfonyl chloride. Yellow crystals. $^1$H NMR: 8.48 (dd, J 6.8 and 2.0 Hz, 2H), 8.22 (dd, J 6.8 and 2.0 Hz, 2H), 7.53-7.47 (m, 2H), 5.07 (d, J 8.0 Hz, 1H), 5.00 (m, 1H), 4.51 (m, 2H), 4.15 (m, 1H), 3.87 (m, 2H), 3.75 (m, 1H), 2.50 (m, 2H). MS: 528 [M+H].

Intermediate 2. 1M LiOBu-t in THF (2.1 mL) was added with stirring to the Intermediate 1 (0.49 g) in THF (4 mL) at ca. 0° C. under nitrogen. The solution was stirred at 0° C. for ca. 15 min, and then at r.t. for ca. 40 min. It was then cooled to ca. −5° C., and the Intermediate 6 (0.91 g) in DMF (4 mL) was added dropwise with stirring, and the mixture was allowed to warm up to r.t. and stirred o.n. AcOH (100 μL) was added, and most of volatiles were removed under vacuum. The residue was taken into EtOAc (ca. 40 mL), washed with 5% aq. NaHCO$_3$ (ca. 3×25 mL), brine, and dried (Na sulfate). The solvent was evaporated under vacuum, and the residue triturated with MTBE-hexanes 1:2 (ca. 50 mL) to afford the crystalline product that was separated and dried under vacuum. MS: 573 [M+H].

Compound of Example 1. The Intermediate 2 was converted into the compound of Example 1 just as described above in Method A (I), isolated as its sodium salt. Off-white solid. $^1$H NMR: 8.43 (d, J 1.6 Hz, 1H), 7.64 (m, 1H), 7.50 (d, J 7.6 Hz, 1H), 6.72 (d, J 1.6 Hz, 1H), 5.06 (d, J 7.6 Hz, 1H), 5.02 (m, 1H), 4.18-4.12 (m, 2H), 3.93-3.82 (m, 4H), 2.51 (m, 2H), 1.95 (s, 3H). MS: 531 [M+H]. MS: 531 [M+H].

Example 2

Compound of Structure

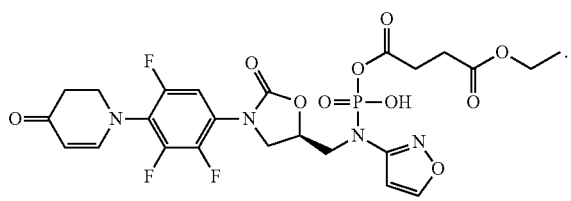 [SMILES: CCOC(=O)CCC(=O)OP(=O)(O)N(C[C@H]1CN(c2cc(F)c(N3C=CC(=O)CC3)c(F)c2F)C(=O)O1)c1ccon1]

Scheme for the compound of Example 2:

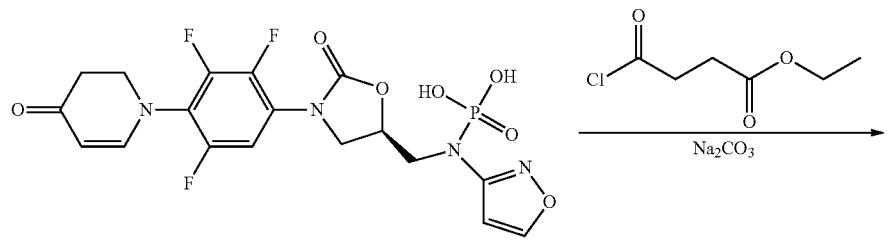

Intermediate 3

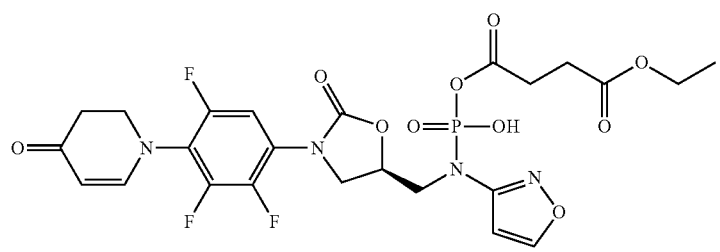

Example 2

Compound of Example 2. The compound of Example 2 was prepared analogously to that described for the Method A for preparation of the compound of Example 1, except using ethyl 4-chloro-4-oxobutanoate instead of Ac$_2$O, and substituting NaOAc for Na$_2$CO$_3$. MS: 617 [M+H].

Example 3

Compound of Structure

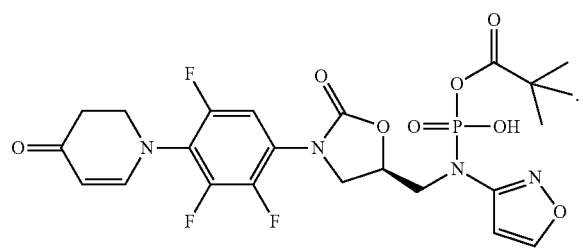 [SMILES: CC(C)(C)C(=O)OP(=O)(O)N(C[C@H]1CN(c2cc(F)c(N3C=CC(=O)CC3)c(F)c2F)C(=O)O1)c1ccon1]

Scheme for the compound of Example 3:

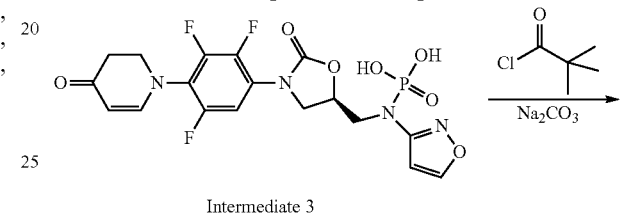

Intermediate 3

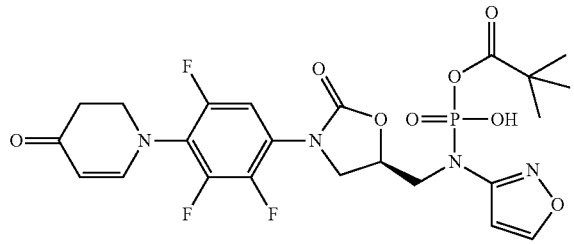

Example 3

Compound of Example 3. The compound of Example 3 was prepared analogously to that described for the Method A for preparation of the compound of Example 1, except using pivaloyl chloride instead of Ac$_2$O, and substituting NaOAc for Na$_2$CO$_3$. MS: 573 [M+H].

Example 4

Compound of Structure

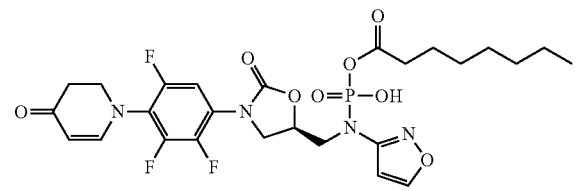

Compound of Example 4. The compound of Example 4 was prepared analogously to that described for the Method A for preparation of the Compound of Example 1, except using octanoyl chloride instead of Ac$_2$O, and substituting NaOAc for Na$_2$CO$_3$. MS: 615 [M+H].

Example 5

Compound of Structure

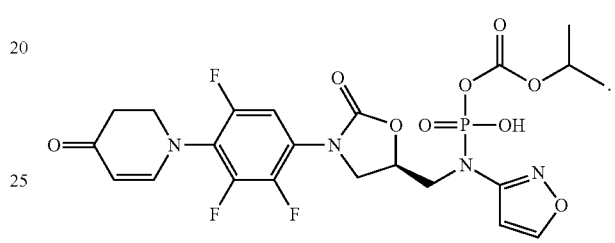

Scheme for the Compound of Example 4:

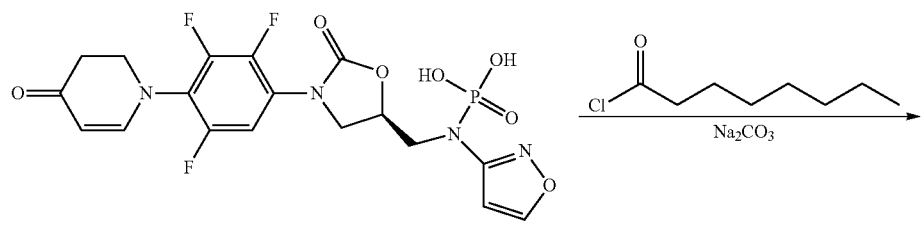

Intermediate 3

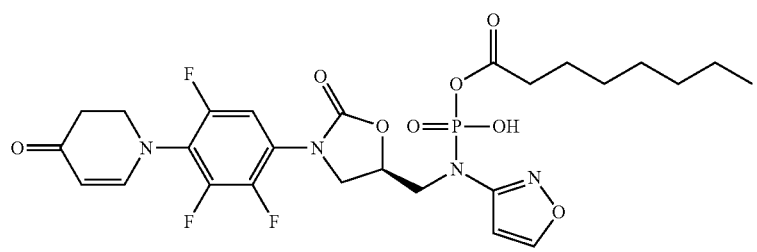

Example 4

Scheme for the compound of Example 5:

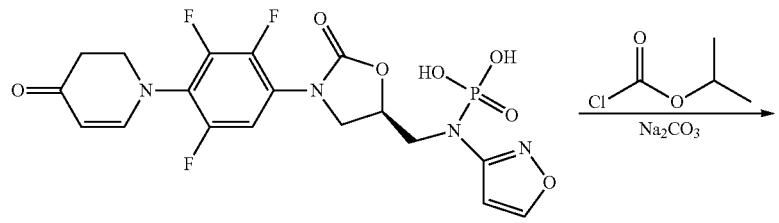

Intermediate 3

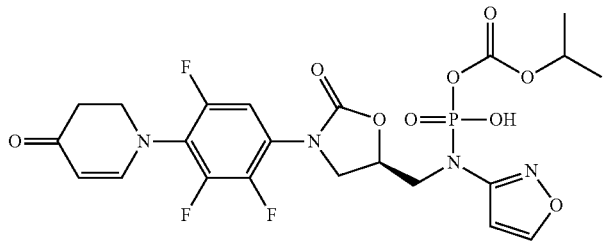

Example 5

Compound of Example 5. The compound of Example 5 was prepared analogously to that described for the Method A for preparation of the compound of Example 1, except using isopropyl chloroformate instead of $Ac_2O$, and substituting NaOAc for $Na_2CO_3$. MS: 575 [M+H].

Intermediate 7. Compound of structure

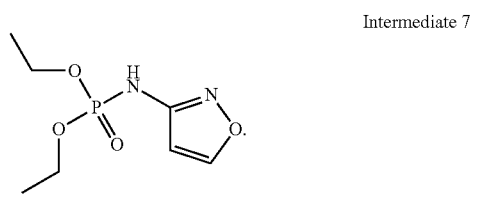

Intermediate 7

Scheme for the compound of Intermediate 7:

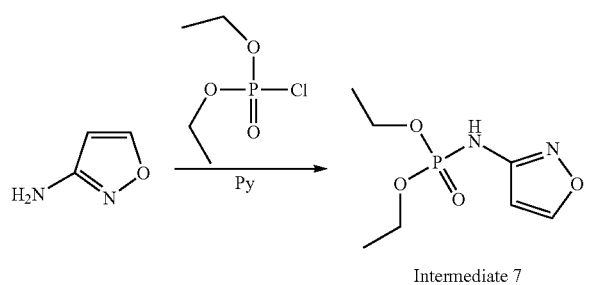

Intermediate 7

Compound of Intermediate 7. The compound of Intermediate 7 was prepared analogously to the procedure for the compound of Intermediate 1 described in the synthesis for compound of Example 1, Method A, except using diethyl chlorophosphate instead of diisopropyl chlorophosphate employed for the synthesis of the compound of Intermediate 1. Colorless oil. MS: 221 [M+H].

Utility and Testing

Oxazolidinone compounds of the subject invention exhibit potent in vivo efficacy against a variety of microorganisms, including gram positive microorganisms. Accordingly, compounds of the subject invention have useful antibacterial activity. Thus, compounds of the present invention are useful antimicrobial agents and may be effective against a number of human and veterinary pathogens, including gram positive aerobic bacteria such as multiply-resistant staphylococci, enterococci, and streptococci, as well as anaerobic microorganisms such as *bacteroides* and clostridia species, and acid-fast microorganisms such as *Mycobacterium tuberculosis* and *Mycobacterium avium*.

To establish useful therapeutic activity of the compounds of present invention, a testing in a mouse peritonitis infection model was performed following general procedures described by Marra et al. in Current Protocols in Pharmacology (2005), 13A.4.1-13A.4.13.

In this mouse infection model with *Staphylococcus aureus* strain SAU1018, the compounds of Examples 1 and 2 exhibited high in vivo activity with $ED_{50}$ (effective dose for survival of 50% of animals in the study) value of 10 mg/kg for each of the compounds, when administered to infected animals via intravenous injection of these agents (sodium salts) in a in a saline solution, which is suitable for a clinical or therapeutic use. This efficacy was identical to that for the parent drug MRX-I control ($ED_{50}$ 10 mg/kg) in the same test, with the latter compound administered to animals in a non-clinical 20% aqueous beta-hydroxypropylcyclodextrin (HPCD) formulation (required for MRX-I dissolution in its non-prodrug form).

The compounds provided herein are also suitable for a convenient oral administration. Thus, when a solution of the compound of Example 1 (sodium salt form) is administered orally to animals in the aforementioned mouse model of *Staphylococcus aureus* infection, high antibacterial efficacy with $ED_{50}$ value of about 8 mg/kg was observed. Above animal test data also illustrate the conversion of the prodrug of Example 1 of this invention into the drug MRX-I in vivo.

In addition, the conversion of prodrugs of this invention into the parent drug MRX-I was tested in the rodent pharmacokinetic (PK) models performed analogously to methods described in the monograph Current Protocols in Pharmacology, 2005, 7.1.1-7.1.26, John Wiley & Sons, Inc. In these tests, the drug is typically detected in the blood, and its amount (concentration) is quantified by liquid chromatography mass-spectroscopy. One critical PK parameter is area-under-the-curve (AUC) derived from the drug concentration—time plot. AUC is the key indicator of the exposure to the test drug. A higher AUC value indicates an elevated drug level, or higher mammal exposure to the drug. A lower AUC value indicates a reduced drug level, or lower mammal exposure to the drug. In case of a prodrug administration, resulted from its in vivo conversion drug is detected and measured (as illustrated, for example, by Bae et al. in J. Pharmacy Pharmacol., 2007, vol. 59. p. 955).

Thus, in a rat model, intravenous administration of the compound of Example 1 (sodium salt form solution in saline, dosed at 10 mg/kg per MRX-I basis) resulted in the drug MRX-I detected in the animal blood, with drug amounts corresponding to AUC value of about 33,420 ng/mL*h. In a side-by-side test, the drug MRX-I administered at same dose (10 mg/kg, solution in 20% aqueous HPCD) was detected in drug amounts corresponding to AUC value of about 25,350 ng/mL*h. Thus, intravenous administration of the prodrug of Example 1 to a test mammal results in its conversion into the parent drug (MRX-I), and with exposure at least similar or even better as compared to the administration of the drug.

The conversion of the compound of Example 1 into the drug MRX-I in vivo proceeds via intermittent formation of a compound of Intermediate 3 as shown in Scheme 4 below.

Scheme 4. In vivo conversion of the prodrug of Example 1 into the drug MRX-I.

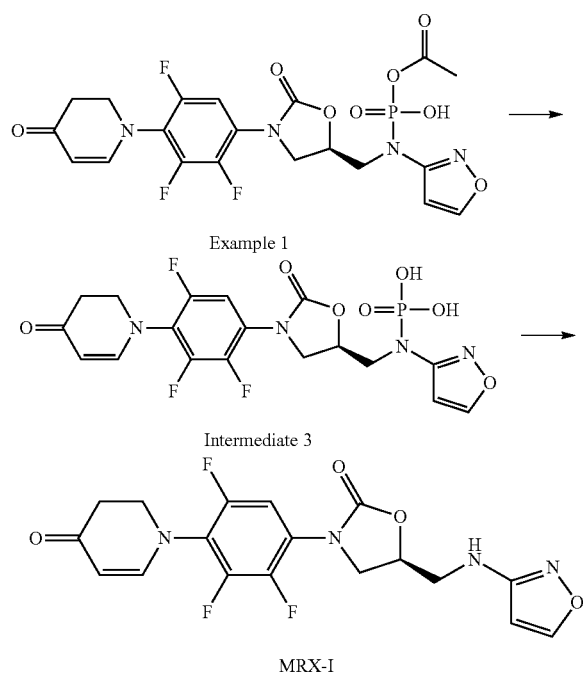

The intermittent formation of the compound of Intermediate 3 in this process was confirmed by detection of this compound in the blood during the rat PK test described above for the compound of Example 1 (after the intravenous administration of latter compound to test animals, resulting in a high exposure to the drug MRX-I). Specifically, the compound of Intermediate 3 was detected by liquid chromatography mass-spectroscopy, based on its characteristic [M+H]$^+$ ion signal with m/z value of 489.08. Thus, the compound of Intermediate 3 itself acts as a prodrug of MRX-I in vivo, and could be used as such. Hence, the compound of Example 1 may be described as a prodrug in relation to the $NPO_3H_2$-compound Intermediate 3, while being "a double prodrug" of the drug MRX-I.

The above observation is in line with the efficacy ($ED_{50}$) test data for the compound of Intermediate 3. The latter exhibited $ED_{50}$ value of about 10 mg/kg in the mouse model of *Staphylococcus aureus* infection (strain SAU1018; performed just as described above for testing of compounds of Examples 1 and 2; administered as a sodium salt saline solution).

In addition, the aqueous solubility testing using HPLC quantitation method with UV detection at 326 nm was performed, as exemplified for the compound of Example 1 below. An aliquot (about 0.3 mL) of a diluent (such as water, 5% dextrose in water (D5W), or same adjusted to a given pH by adding small amounts of an acid, such as HCl or lactic acid) was added to a test compound (about 0.9 g), and this mixture was agitated overnight at r.t. At time points of 2 and 24 h, each test vial was centrifuged (10,000 rpm), the precipitate-free supernatant sampled, diluted (10,000-fold) with a diluent (same as above), and this solution was then analyzed by HPLC. The concentration of the compound in test solution was determined by comparing UV detection AUC values for the diluted sample against the standard calibration curve, and then the concentration of the original undiluted solution was calculated, taking into account the dilution factor.

The testing data reveal a surprisingly high solubility of the compound of Example 1 (sodium salt) in aqueous solutions. This compound exhibited an exceptional solubility of about 400 mg/mL in D5W at pH 5, in absence of any specialized additives or excipients, such as organic solvents or complexing agents, such as HPCD. Likewise, the compound of Example 2 exhibited high aqueous solubility of at least 20 mg/mL.

Importantly, these solubility values are dramatically higher than the same for the parent drug of these prodrug compounds, the clinical agent MRX-I. For the latter drug, a solubility of only about 0.25 mg/mL could be attained in water or conventional aqueous solutions (when tested using the procedure analogous to that described for the prodrug, with HPLC quantitation and UV detection at 326 nm). It is also well above the solubility value of about 3 mg/mL reported for the oxazolidinone drug linezolid (see Prescribing Information for Zyvox, Pfizer, LAB-0139-20.0, Revised June 2010). The latter solubility limitation of linezolid requires a 300 cc intravenous bag for administration of its single dose of 600 mg (which is not at all possible for much less soluble agent MRX-I).

Thus, the compounds invented herein offer a significant benefit with respect to much more convenient administration (to a mammal in need of a therapy) in a small volume (for example, 50 cc or 100 cc), such as shorter duration intravenous infusion, or fast bolus injection which does not require specialized medical equipment (needed for an infusion).

The fast bolus administration is particularly useful for an outpatient care, or for emergency therapy, or for emergency treatment to prevention an infection (for example, following an accidental exposure to a pathogen).

Furthermore, the compounds provided herein could be conveniently stored in a solid form, and then dissolved in a suitable diluent just before the administration. This eliminates inconvenience and additional cost of the manufacture, storage, and transportation of pre-dissolved drug solutions (such as required, for example, for 300 cc intravenous bags of linezolid). In addition, the risk of the drug precipitation from pre-formulated solution (for example, due to inadequate temperature control during storage or transportation) is also obviated.

In aqueous stability testing (performed just as described above for the solubility testing, with alike HPLC UV detection of the compound signal, and test compound concentration determination at different time points), no significant degradation and precipitation was observed for the compounds of Examples 1 and 2 at pH range of about 4-5 over at least 4-6 h. Thus, only minimal degradation of the compound of Example 1 (sodium salt form) was observed in D5W solution at pH 5 over 24 h at r.t., and without apparent precipitation. Alike (D5W at media pH 5) solutions of drugs are commonly used for intravenous, subcutaneous, intramuscular, or oral drugs administration. Consequently, the stability of these compounds in the clinically acceptable aqueous solution validates the suitability of new prodrugs provided herein for intravenous or oral administration.

The aqueous stability of compounds provided herein is entirely unexpected, since their O-carbonyl-phosphoramidate structure is similar to a substructure R(C=O)—O—P(=O) present in mixed phosphate-carboxylate anhydrides. Due to high reactivity of such mixed anhydrides, these are not isolated but generated in situ, and used for acyl R(C=O) transfer reactions (for example, amides formation described by McNulty in Tetrahedron, 2012, vol. 68, p. 5415). In contrast, the compounds of this invention are surprisingly stable in aqueous solutions, and are well tolerated when administered to a test mammal (as illustrated by the aforementioned $ED_{50}$ efficacy tests for the mouse model, and also by additional 14-days repeated dose testing in a rat).

Thus, the testing data demonstrate that certain compounds of this invention exhibit excellent therapeutic activity in vivo, while also greatly improving the solubility as compared to the parent agents (lacking the O-carbonyl phosphoramidate prodrug group), allowing for a facile drug administration in form of stable clinically acceptable aqueous solutions, and at the high drug concentration.

Administration and Pharmaceutical Formulations

In general, the compounds of the subject invention can be administered in a therapeutically effective amount by any of the accepted modes of administration for agents that serve similar utilities. By way of example, compounds of the subject invention may be administered orally, parenterally, transdermally, topically, rectally, or intranasally. The actual amount of a compound of the subject invention, i.e., the active ingredient, will depend on a number of factors, such as the severity of the disease, i.e., the infection, to be treated, the age and relative health of the subject, the potency of the compound used, the route and form of administration, and other factors, all of which are within the purview of the attending clinician.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from animal models. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans.

When employed as pharmaceuticals, the compounds of the subject invention are usually administered in the form of pharmaceutical compositions. These compounds can be administered by a variety of routes including oral, parenteral, transdermal, topical, rectal, and intranasal.

Compounds provided herein are effective as injectable, oral, inhalable, or topical compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions are preferably formulated in a unit dosage form, each dosage containing from about 0.1 to about 3000 mg, more usually about 1 to about 900 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

An active compound is effective over a wide dosage range and is generally administered in a pharmaceutically or therapeutically effective amount. It, will be understood, however, that the amount of the compound actually administered can be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, compounds or pharmaceutical compositions thereof can be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 mg/kg to about 250 mg/kg, more preferably about 1.0 mg/kg to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

Other suitable formulations for use in the present invention can be found in *Remington's Pharmaceutical Sciences*, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The disclosures of each and every patent, patent application and publication (for example, journals, articles and/or textbooks) cited herein are hereby incorporated by reference in their entirety. Also, as used herein and in the appended claims, singular articles such as "a", "an" and "one" are intended to refer to singular or plural. While the present invention has been described herein in conjunction with a preferred aspect, a person with ordinary skills in the art, after reading the foregoing specification, can affect changes, substitutions of equivalents and other types of alterations to the invention as set forth herein. Each aspect described above can also have included or incorporated therewith such variations or aspects as disclosed in regard to any or all of the other aspects. The present invention is also not to be limited in terms of the particular aspects described herein, which are intended as single illustrations of individual aspects of the invention. Many modifications and variations of this invention can be made without departing from its spirit and scope, as will be apparent to those skilled in the art. Functionally equivalent methods within the scope of this invention, in addition to those enumerated herein, will be apparent to those skilled in the art from the foregoing descriptions. It is to be understood that this invention is not limited to particular methods, reagents, process conditions, materials and so forth, which can, of course, vary. It is also to be understood that the terminology used herein is for the purpose of describing particular aspects only, and is not intended to be limiting. Thus, it is intended that the specification be considered as exemplary.

What is claimed is:

1. A compound of the following formula I

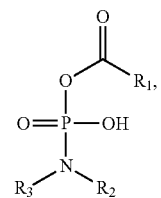

or a pharmaceutically acceptable salt or solvate thereof, wherein:

$R^1$ is H, $C_{1-20}$alkyl, $C_{3-6}$cycloalkyl, $C_{2-4}$alkenyl, $C_{2-4}$alkynyl, $C_{1-4}$heteroalkyl, aryl, heteroaryl, $Het^1$, $Het^2$, C(=O)$C_{1-4}$alkyl, C(=O)OH, C(=O)O$C_{1-4}$alkyl, $(CH_2)_mC(=O)OH,(CH_2)_mC(=O)C_{1-4}$alkyl, $(CH_2)_mC(=O)OC_{1-4}$alkyl, $NH_2$, $NHC_{1-4}$alkyl, $N(C_{1-4}$alkyl)$_2$N($C_{1-4}$alkyl)(aryl), O$C_{1-4}$alkyl, S$C_{1-4}$alkyl, $(CH_2)_mC_{3-6}$cycloalkyl, $(CH_2)_mC(=O)$-aryl, or $(CH_2)_mC(=O)$-$Het^1$;

m is 0, 1, or 2;

$R_2$ is selected from H, $C_{1-20}$alkyl, $C_{3-6}$cycloalkyl, $C_{2-4}$alkenyl, $C_{2-4}$alkynyl, $C_{1-20}$heteroalkyl, aryl, heteroaryl, [3-(2,3,5-trifluoro-4-(4-oxo-3,4-dihydropyridin-1(2H)-yl)phenyl)oxazolidin-2-one-5-yl]methyl, [3-(3-fluoro-4-morpholinophenyl)oxazolidin-2-one-5-yl]methyl, [3(3-fluoro-4-(6-(2-methyl-2H-tetrazol-5-yl)pyridine-3-yl)phenyl)-oxazolidin-2-one-5-yl]methyl, [3-(3-fluoro-4-(6-(1-methyl-1H-tetrazol-5-yl)pyridin-3-yl)phenyl)-oxazolidin-2-one-5-yl]methyl, $Het^1$, $Het^2$, C(=O)$C_{1-4}$alkyl, $(CH_2)_mC(=O)C_{1-4}$alkyl, $(CH_2)_mC_{3-6}$cycloalkyl, $(CH_2)_mC(=O)$-aryl, and$(CH_2)_mC(=O)$-$Het_1$;

$R^3$ is selected from $C_{1-20}$alkyl, $C_{3-6}$cycloalkyl, $C_{2-4}$alkenyl, $C_{1-20}$heteroalkyl, aryl, heteroaryl, [3-(2,3,5-trifluoro-4-(4-oxo-3,4-dihydropyridin-1(2 H)-yl)phenyl)oxazolidin-2-one-5-yl]methyl, [3-(3-fluoro-4-morpholinophenyl)oxazolidin-2-one-5-yl]methyl, [3-(3-fluoro-4-(6-(2-methyl-2H-tetrazol-5-yl)pyridin-3-yl)phenyl)-oxazolidin-2-one-5-yl ]methyl, [3-(3-fluoro-4-(6-(1-methyl-1H-tetrazol-5-yl)pyridine-3-yl)

phenyl)-oxazolidin-2-one-5-yl]methyl, Het¹, Het², C(=O)C$_{1-4}$alkyl, (CH$_2$)$_m$C(=O)C$_{1-4}$alkyl, (CH$_2$)$_m$C$_{3-6}$cycloalkyl, (CH$_2$)$_m$C(=O)-aryl, and (CH$_2$)$_m$C(=O)-Het¹; wherein the C$_{1-20}$ alkyl in R$_3$ is optionally substituted with one, two, or three substituents selected from the group consisting of aryl, Het¹, and Het²;

each Het¹ is independently a C-linked, five or six-membered, monocyclic or bicyclic heterocyclic ring which is aromatic, saturated, or unsaturated and comprises 1, 2, 3, or 4 heteroatoms selected from the group consisting of oxygen, nitrogen, and S(O)$_n$ within the ring and where the remaining atoms are carbon; and where Het¹ is optionally substituted with 1, 2, or 3 groups independently selected from oxo, aryl, halo, CN, —C$_{1-4}$alkyl, —OH, —OC$_{1-4}$alkyl, —S(O)$_n$C$_{1-4}$alkyl, —C$_{1-4}$alkylNH$_2$, —NHC$_{1-4}$ alkyl, —C(=O)H, and —C=N—OR$_d$;

each Het² is independently an N-linked, five or six-membered, monocyclic or bicyclic heterocyclic ring which is aromatic, saturated, or unsaturated and comprises 1, 2, 3, or 4 nitrogen atoms and optionally comprises one oxygen or sulfur atom, and where the remaining atoms are carbon; and where Het² is optionally substituted with 1, 2, or 3 groups independently selected from oxo, aryl, halo, CN, —C$_{1-4}$ alkyl, —OH, —OC$_{1-4}$alkyl, —S(O)$_n$C$_{1-4}$alkyl, —C$_{1-4}$alkylNH$_2$—NHC$_{1-4}$alkyl, —C(=O)H, and —C=N—OR$_d$;

n is 0, 1, or 2; and

R$_d$ is hydrogen or C$_{1-4}$alkyl.

2. A compound of formula II

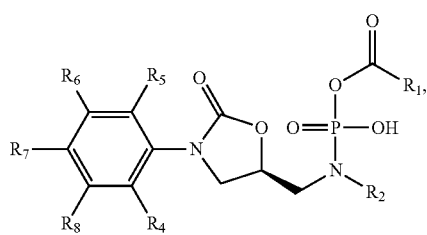

or a pharmaceutically acceptable salt thereof wherein:

R¹ is H, C$_{1-20}$alkyl, C$_{3-6}$cycloalkyl, C$_{2-4}$alkenyl, C$_{2-4}$alkynyl, C$_{1-4}$heteroalkyl, aryl, heteroaryl, Het¹, Het², C(=O)C$_{1-4}$alkyl, C(=O)OH, C(=O)OC$_{1-4}$alkyl, (CH$_2$)$_m$C(=O)OH, (CH$_2$)$_m$C(=O)C$_{1-4}$alkyl, (CH$_2$)$_m$C(=O)OC$_{1-4}$alkyl, NH$_2$NHC$_{1-4}$alkyl, N(C$_{1-4}$alkyl)$_2$, N(C$_{1-4}$alkyl)(aryl), OC$_{1-4}$alkyl, SC$_{1-4}$ alkyl, (CH$_2$)$_m$C$_{3-6}$cycloalkyl, (CH$_2$)$_m$ C(=O)aryl, or (CH$_2$)$_m$ C(=O)-Het¹;

each Het¹ is independently a C-linked, five or six-membered, monocyclic or bicyclic heterocyclic ring which is aromatic, saturated, or unsaturated and comprises 1, 2, 3, or 4 heteroatoms selected from the group consisting of oxygen, nitrogen, and S(O)$_n$ within the ring and where the remaining atoms are carbon; and where Het¹ is optionally substituted with 1, 2, or 3 groups independently selected from oxo, aryl, halo, CN, —C$_{1-4}$alkyl, —OH, —OC$_{1-4}$ alkyl, —S(O)$_n$ C$_{1-4}$alkyl, —C$_{1-4}$alkylNH$_2$, —NHC$_{1-4}$alkyl, —C(=O)H, and —C=H, and —C=N—OR$_d$; and each Het² is independently an N-linked, five or six-membered, monocyclic or bicyclic heterocyclic ring which is aromatic, saturated, or unsaturated and comprises 1, 2, 3, or 4 nitrogen atoms and optionally comprises one oxygen or sulfur atom, and where the remaining atoms are carbon; and where Het² is optionally substituted with 1, 2, or 3 groups independently selected from oxo, aryl, halo, CN, —C$_{1-4}$alkyl, —OH, —OC$_{1-4}$alkyl, —S(O)$_n$ C$_{1-4}$alkyl, —C$_{1-4}$alkylNH$_2$, —NHC$_{1-4}$alkyl, —C(=O)H, and —C=N—OR$_d$;

n is 0, 1, or 2;

R$_d$ is hydrogen or C$_{1-4}$alkyl;

R² is isoxazol-3-yl optionally substituted with 1 R⁹; C(=O)C$_{1-4}$alkyl; (CH$_2$)$_m$C(=O)C$_{1-4}$alkyl; (CH$_2$)$_m$C$_{3-6}$cycloalkyl; (CH$_2$)$_m$C(=O)-aryl; or (CH$_2$)$_m$C(=O)-Het¹;

m is 0, 1, or 2;

R⁴ and R⁵ are independently H or F;

R⁶ and R⁸ are independently H, F, Cl, or CN;

R⁷ is C$_{3-6}$cycloalkyl, aryl, biaryl, Het¹, Het², or 4 to 7-membered heterocyclic group; or R⁶ and R⁷ taken together form a 4 to 7-membered heterocyclic group fused onto the benzene ring; and R⁹ is H, C$_{1-6}$alkyl, halo, or CN.

3. The compound of claim 2 according to formula II, wherein R⁴, R⁵, R⁶, and R⁸ are independently selected from H and F, and R⁷ is morpholino, 2,3-dihydropyridin-4(1H)-one-1-yl, 4-cyanopyridyl, 2-(2-methyl-2H-tetrazol-5-yl)pyridine-5-yl, 2-(1-methyl-1H-tetrazol-5-yl)pyridine-5-yl, 4-[N-(1H-1,2,3-triazol-5-yl)methylaminomethyl]phenyl, 1-methyl-1,4,5,6-tetrahydro-1,2,4-triazin-4-yl, or 5,6-dihydro-1,2,4-oxadiazin-4-yl.

4. The compound of claim 2 according to formula III

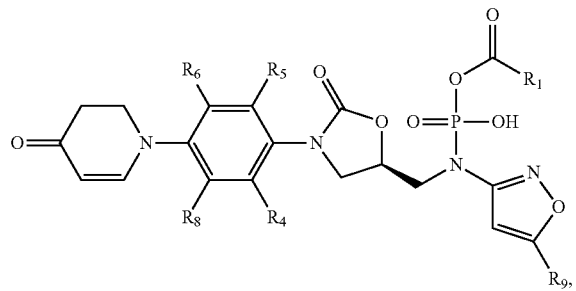

or a pharmaceutically acceptable salt or solvate thereof.

5. The compound of claim 2, wherein R¹ is C$_{1-8}$alkyl, (CH$_2$)$_m$C(=O)OC$_{1-4}$alkyl, NHC$_{1-4}$alkyl, N(C$_{1-4}$alkyl)$_2$, aryl, or Het².

6. The compound of claim 4 selected from the structures:

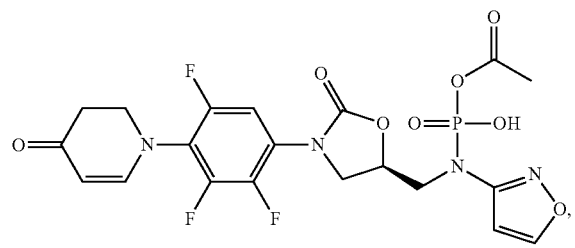

7. The compound of claim 4 selected from the structures:

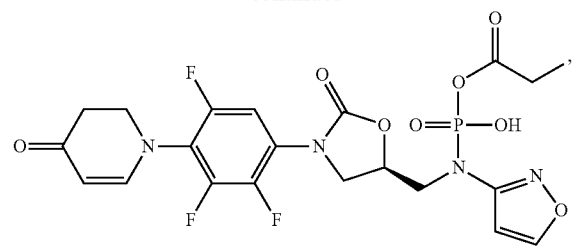

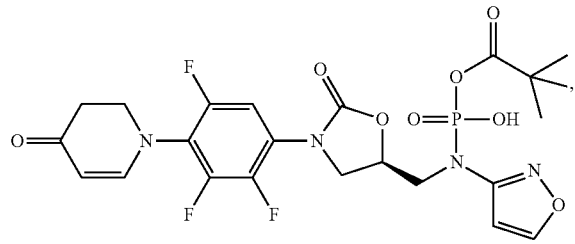

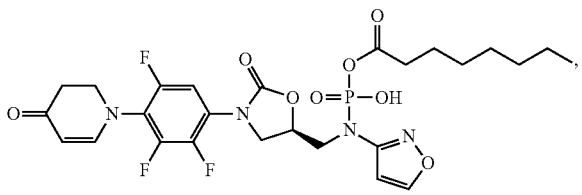

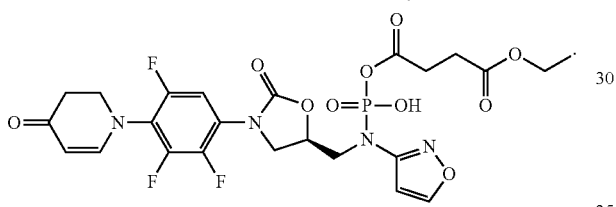

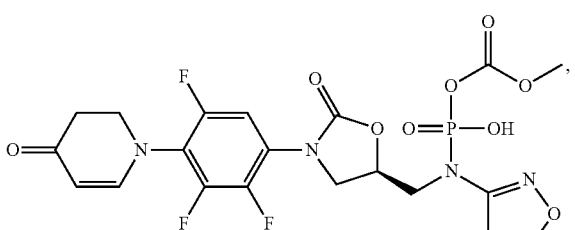

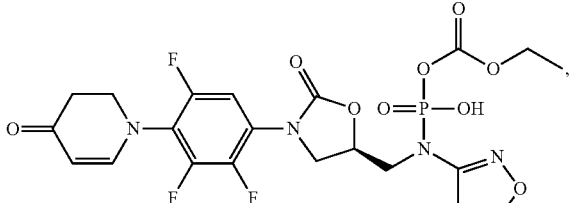

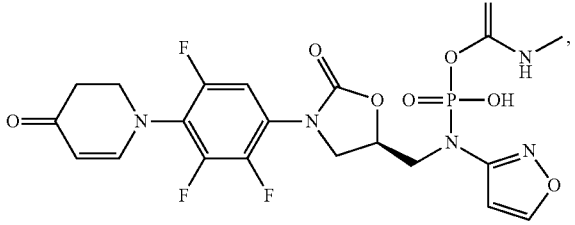

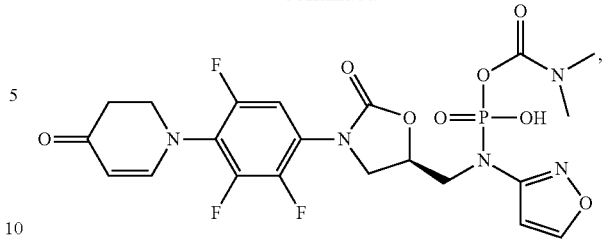

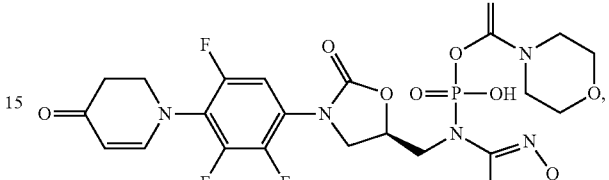

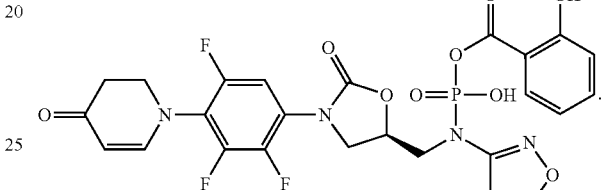

8. A compound of formula V:

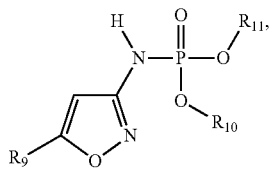

wherein:
$R^9$ is H, $C_{1-6}$alkyl, halo, or CN; and
$R^{10}$ and $R^{11}$ are independently selected from $C_{1-20}$alkyl and $C_{3-6}$cycloalkyl, or $R^{10}$ and $R^{11}$ taken together is $C_{1-20}$alkylidene group.

9. The compound of claim 8, wherein $R^9$ is H, and both $R^{10}$ and $R^{11}$ are $C_{1-20}$alkyl.

10. A pharmaceutical composition comprising a therapeutically effective amount of a compound of claim 2 and a pharmaceutically acceptable carrier.

11. A pharmaceutical composition comprising a therapeutically effective amount of a compound of claim 6 and a pharmaceutically acceptable carrier.

12. A pharmaceutical composition comprising a therapeutically effective amount of a compound of claim 7 and a pharmaceutically acceptable carrier.

13. A method for the treatment of a microbial infection in a mammal comprising administering to the mammal in need thereof a therapeutically effective amount of a compound of claim 2.

14. The method according to claim 13, wherein the compound is administered to the mammal orally, parenterally, transdermally, topically, rectally, or intranasally.

15. The method according to claim 13, wherein the compound is administered as a water-based solution and at said compound concentration from about 50 mg/mL to about 400 mg/mL.

16. The method according to claim 13, wherein the compound is administered in a daily dose of from about 1 to about 75 mg/kg.

17. A method for the treatment of a microbial infection in a mammal comprising administering to the mammal in need thereof a therapeutically effective amount of a compound of claim 6.

18. A method for the treatment of a microbial infection in a mammal comprising administering to the mammal in need thereof a therapeutically effective amount of a compound of claim 7.

19. A method for the treatment of a microbial infection in a mammal comprising administering to the mammal in need thereof a therapeutically effective amount of a pharmaceutical composition of claim 12.

* * * * *